(12) United States Patent
Follmann et al.

(10) Patent No.: US 8,835,653 B2
(45) Date of Patent: Sep. 16, 2014

(54) CHLOROTHIOPHENE-ISOXAZOLES AS INHIBITORS OF COAGULATION FACTORS XA AND THROMBIN

(75) Inventors: Markus Follmann, Wülfrath (DE); Volkmar Wehner, Frankfurt am Main (DE); Jean-Michel Altenburger, Paris (FR); Gilbert Lassalle, Paris (FR); Jean-Pascal Herault, Paris (FR)

(73) Assignee: Sanofi, Paris (FR)

( * ) Notice: Subject to any disclaimer, the term of this patent is extended or adjusted under 35 U.S.C. 154(b) by 674 days.

(21) Appl. No.: 12/858,981

(22) Filed: Aug. 18, 2010

(65) Prior Publication Data

US 2011/0112074 A1    May 12, 2011

Related U.S. Application Data

(63) Continuation of application No. PCT/EP2009/000902, filed on Feb. 10, 2009.

(30) Foreign Application Priority Data

Feb. 21, 2008  (EP) .................................. 08290166

(51) Int. Cl.
| | |
|---|---|
| C07D 413/14 | (2006.01) |
| A61K 31/55 | (2006.01) |
| A61P 9/10 | (2006.01) |
| A61P 7/02 | (2006.01) |
| A61K 31/454 | (2006.01) |
| A61K 31/496 | (2006.01) |
| A61K 31/5377 | (2006.01) |
| C07D 413/04 | (2006.01) |

(52) U.S. Cl.
CPC ............ C07D 413/14 (2013.01); C07D 413/04 (2013.01)
USPC ........ 549/29; 548/240; 514/217.05; 514/326; 514/254.04; 514/253.1; 514/236.8; 540/298; 549/209; 544/364

(58) Field of Classification Search
None
See application file for complete search history.

(56) References Cited

U.S. PATENT DOCUMENTS 6,274,620 B1 *  8/2001  Labrecque et al. ........... 514/448
6,313,242 B1 * 11/2001  Reddy ........................... 526/160
2006/0100216 A1 *  5/2006  Askew et al. ............ 514/254.05

FOREIGN PATENT DOCUMENTS

WO    WO 01/38309    * 5/2001

OTHER PUBLICATIONS

Spyropolous in Expert Opinion in Investigative Drugs (2007) 16(4):431-440.*
J. G. Cannon Chapter Nineteen in Burger's Medicinal Chemistry and Drug Discovery, Fifth Edition, vol. I: Principles and Practice, Wiley-Interscience 1995, pp. 783-802, 784.*
Schafer et al. Drug Discovery Today 2008, 13 (21/22), 913-916.*
Dörwald in Side Reaction in Organic Synthesis.*
Patani et al. in Chemical Reviews 1996, 96, 3147-3176.*
Falorni et al. in Tetrahedron Letters 39(1998), 9241-9244).*
Dörwald in Side Reaction in Organic Synthesis (2005), Wiley-VCH Verlag GmbH & Co. Weinheim.*

* cited by examiner

Primary Examiner — Dennis Heyer
(74) Attorney, Agent, or Firm — Scully, Scott, Murphy & Presser, P.C.

(57) ABSTRACT

The present invention relates to compounds of the formula I,

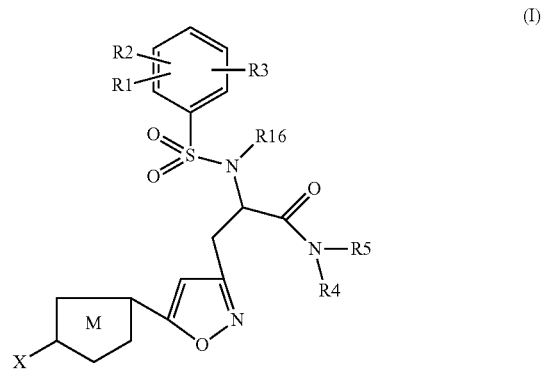

wherein R1; R2; R3; R4; R5, R16, X and M have the meanings indicated in the claims. The compounds of formula I are valuable pharmacologically active compounds. They exhibit a strong anti-thrombotic effect and are suitable, for example, for the therapy and prophylaxis of cardio-vascular disorders like thromboembolic diseases or restenoses. They are reversible inhibitors of the blood clotting enzymes factor Xa and thrombin and can in general be applied in conditions in which an undesired activity of factor Xa and/or thrombin are present or for the cure or prevention of which an inhibition of factor Xa and thrombin are intended. The invention furthermore relates to processes for the preparation of compounds of the formula I, their use, in particular as active ingredients in pharmaceuticals, and pharmaceutical preparations comprising them.

14 Claims, No Drawings

CHLOROTHIOPHENE-ISOXAZOLES AS INHIBITORS OF COAGULATION FACTORS XA AND THROMBIN

FIELD OF THE INVENTION

The present invention relates to compounds of the formula I,

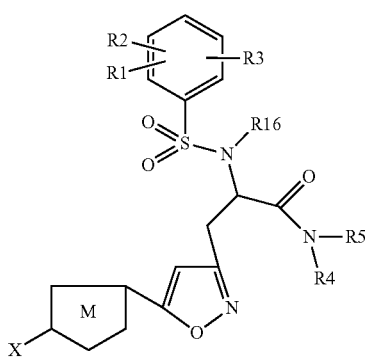

wherein R1; R2; R3; R4; R5, R16, X and M have the meanings indicated below. The compounds of formula I are valuable pharmacologically active compounds. They exhibit a strong anti-thrombotic effect and are suitable, for example, for the therapy and prophylaxis of cardio-vascular disorders like thromboembolic diseases or restenoses. They are reversible inhibitors of the blood clotting enzymes factor Xa (FXa) and thrombin and can in general be applied in conditions in which an undesired activity of factor Xa and/or thrombin are present or for the cure or prevention of which an inhibition of factor Xa and thrombin are intended. The invention furthermore relates to processes for the preparation of compounds of the formula I, their use, in particular as active ingredients in pharmaceuticals, and pharmaceutical preparations comprising them.

BACKGROUND OF THE INVENTION

Normal haemostasis is the result of a complex balance between the processes of clot initiation, formation and clot dissolution. The complex interactions between blood cells, specific plasma proteins and the vascular surface maintain the fluidity of blood unless injury and blood loss occurs. Many significant disease states are related to abnormal haemostasis e.g. local thrombus formation due to rupture of atherosclerotic plaque is a major cause of acute myocardial infarction and unstable angina. Treatment of an occlusive coronary thrombus by either thrombolytic therapy or percutaneous angioplasty may be accompanied by acute thrombolytic reclosure of the affected vessel.

Thrombotic diseases remain one of the leading causes of death in developed countries despite the availability of anticoagulants such as warfarin, heparin and low molecular weight heparins, and antiplatelet agents such as aspirin and clopidogrel. The oral anticoagulant warfarin inhibits the post-translational maturation of coagulation factors VII, IX, and X and prothrombin and has proven effective in both venous and arterial thrombosis. However, warfarin's usage is limited because of its narrow therapeutic index, slow onset of therapeutic effect, numerous dietary and drug interactions, and a need for monitoring and dose adjustment. This not withstanding, warfarin remains the standard orally administered anticoagulant available. Patients on warfarin therapy require regular monitoring in part because of its narrow therapeutic index and interactions with food and other drugs. Injectable agents that are also widely used include low molecular weight heparins and the synthetic pentasaccharide fondaparinux. Thus, discovering and developing safe and efficacious oral anticoagulants for the prevention and treatment of a wider range of thrombotic diseases has become increasingly important.

A key strategy for the discovery and development of new anticoagulants has been the targeting of specific enzymes within the blood coagulation cascade. One approach is to inhibit thrombin and thrombin generation by targeting the inhibition of coagulation factor Xa. Preparations of beta-amino acid-, aspartic acid- and diaminopropionic-benzamides or preparations of heterocycles containing ethylenediamine moiety as activated blood coagulation factor Xa inhibitors were described in International Patent Applications WO 01/038309 and WO 2004/058728.

Factor Xa, a trypsin-like serine protease, is crucial to the conversion of prothrombin to thrombin, the final enzyme in the coagulation cascade that is responsible for fibrin clot formation. Animal models have suggested that inhibiting FXa and/or thrombin has the potential for providing excellent antithrombotic efficacy. Even more it has been suggested that dual inhibitors could result in an improved activity when compared to single point inhibition of the coagulation cascade.

DESCRIPTION OF THE INVENTION

The present invention satisfies the above needs by providing compounds of formula I, which exhibit both factor Xa and thrombin inhibitory activity.

Thus, the present invention relates to compounds of the formula I,

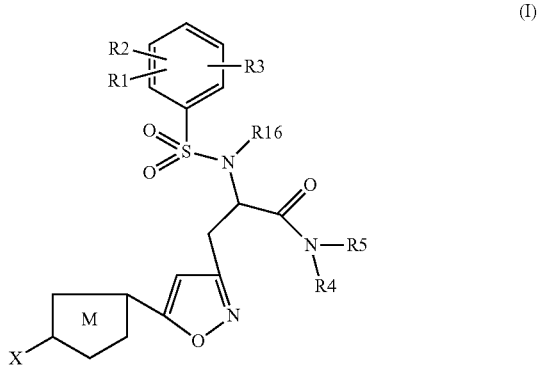

wherein

is a thiophenyl residue,
X is halogen, methyl or ethynyl,
R1, R2 and R3 are independent of one another are identical or different and are a hydrogen atom, —($C_0$-$C_3$)-alkylene-C(O)—R10, —($C_0$-$C_3$)-alkylene-C(O)—NH—R6, —($C_0$-

$C_3$)-alkylene-C(O)—N(R21)-R22, —($C_0$-$C_3$)-alkylene-C(O)—O—R10, halogen, —O—($C_1$-$C_4$)-alkyl, —O—($C_1$-$C_3$)-fluoroalkyl, —($C_0$-$C_4$)-alkylene-($C_1$-$C_3$)-fluoroalkyl, —($C_1$-$C_3$)-alkylene-S(O)—R10, —($C_0$-$C_5$)-alkylene-S(O)$_2$—N(R14)-R15, —($C_1$-$C_3$)-alkylene-S(O)$_2$—R10, —($C_0$-$C_5$)-alkylene-($C_3$-$C_8$)-cycloalkyl-R23, —($C_1$-$C_4$)-alkyl, wherein alkyl is unsubstituted or substituted one, two or three times by R8, —($C_0$-$C_4$)-alkylene-aryl, wherein aryl is selected out of the group phenyl, naphthyl, biphenylyl, anthryl or fluorenyl, wherein aryl is mono-, di- or trisubstituted independently of one another by R8, or —($C_0$-$C_4$)-alkylene-heterocyclyl, wherein heterocyclyl is selected out of the group acridinyl, azabenzimidazolyl, azaspirodecanyl, azepinyl, azetidinyl, aziridinyl, benzimidazolyl, 1,3-benzodioxolyl, benzofuranyl, benzothienyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydro-oxa-zolinyl, dioxazolyl, dioxinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phenylpyridyl, phthalazinyl, piperazinyl, piperidinyl, pteridinyl, purinyl, pyranyl, pyrazinyl, pyrazolidinyl, pyrazolinyl, pyrazolyl, pyridazinyl, pyridoimidazolyl, pyridooxazolyl, pyridopyrimidinyl, pyridothiazolyl, pyridothienyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinolyl, quinoxalinyl, quinuclidinyl, tetrahydrofuranyl, tetrahydroisoquinolinyl, tetrahydroquinolinyl, 1,4,5,6-tetrahydro-pyridazinyl, tetrahydropyranyl, tetrahydropyridinyl, tetrahydro-thiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,4-triazolyl, 1,2,5-triazolyl, 1,3,4-triazolyl and xanthenyl, and wherein said heterocyclyl is unsubstituted or mono-, di- or trisubstituted independently of one another by R8, R4 and R5 are the same or different and are independently of one another
1) hydrogen atom,
2) —($C_1$-$C_6$)-alkyl, wherein alkyl is unsubstituted or mono-, di- or trisubstituted independently of one another by R7,
3) —($C_0$-$C_6$)-alkylene-($C_3$-$C_8$)-cycloalkyl,
4) —SO$_t$—R10, wherein t is 1 or 2,
5) —($C_0$-$C_6$)-alkylene-aryl, wherein aryl is as defined above and alkylene and aryl independently from one another are unsubstituted or mono-, di- or trisubstituted by R7,
6) —($C_1$-$C_3$)-fluoroalkyl,
7) —O—($C_1$-$C_4$)-alkyl or
8) —($C_0$-$C_6$)-alkylene-heterocyclyl, wherein heterocyclyl is as defined above and alkylene and heterocyclyl independently from one another are unsubstituted or mono-, di- or trisubstituted by R7, provided that R4 and R5 are not each a hydrogen atom, or R4 and R5 together with the nitrogen atom to which they are bonded form a 4- to 10-membered mono- or bicyclic heterocyclic ring which in addition to the nitrogen atom can contain one, two or three identical or different ring heteroatoms chosen from oxygen, sulfur and nitrogen, wherein said heterocyclic ring is unsubstituted or mono-, di- or trisubstituted independently of one another by R7, R6 is 1) heterocyclyl, wherein heterocyclyl is as defined above and is un-substituted or mono-, di- or tri substituted independently of one another by R8 or 2) aryl, which is as defined above wherein aryl is unsubstituted or mono-, di- or trisubstituted independently of one another by R8, R7 is halogen, —NO$_2$, =O, —CF$_3$, —($C_0$-$C_3$)-alkylene-C(O)—O—R10, —C(O)—R10, —CN, —OH, —NH$_2$, —C(O)—N(R10)-R20, —N(R10)-R20, =F$_2$, —O—($C_1$-$C_3$)-fluoroalkyl, —($C_0$-$C_4$)-alkylene-($C_1$-$C_3$)-fluoroalkyl, —($C_0$-$C_3$)-alkylene-($C_3$-$C_8$)-cycloalkyl, —($C_1$-$C_8$)-alkyl, wherein alkyl is unsubstituted or mono-, di- or trisubstituted independently of one another by halogen, NH$_2$, —OH or —O—($C_1$-$C_6$)-alkyl, —O—($C_1$-$C_6$)-alkyl, wherein alkyl is unsubstituted or mono-, di- or trisubstituted independently of one another by halogen, NH$_2$, —OH or a methoxy residue, or —($C_0$-$C_3$)-alkylene-heterocyclyl, wherein heterocyclyl is as defined above and is unsubstituted mono-, di- or trisubstituted independently of one another by R10, R8 is halogen, —NO$_2$, —CN, =O, —OH, —CF$_3$, —C(O)—O—R10, —C(O)—N(R21)-R22, —N(R21)-R22, —($C_3$-$C_8$)-cycloalkyl, —($C_0$-$C_3$)-alkylene-O—R10, —Si—(CH$_3$)$_3$, —N(R10)-S(O)$_u$—R10, wherein u is 1 or 2, —S—R10, —SO$_r$—R10, wherein r is 1 or 2, —S(O)$_v$—N(R10)-R20, wherein v is 1 or 2, —C(O)—R10, —($C_1$-$C_8$)-alkyl, —($C_1$-$C_8$)-alkoxy, phenyl, phenyloxy-, —($C_1$-$C_3$)-fluoroalkyl, —O—R9, —($C_0$-$C_4$)-alkyl-C(O)—O—C(R9, R11)-O—C(O)—R12, —NH—C(O)—NH—R10, —NH—C(O)—NH—R6, —N(R21)-C(O)—R22, —O—CF$_3$, —NH—C(O)—O—R10, or —($C_0$-$C_4$)-alkyl-C(O)—O—C(R9, R11)-O—C(O)—O—R12, R9 and R11 are the same or different and are independently of one another hydrogen, —($C_1$-$C_6$)-alkyl, or together with the carbon atom to which they are bonded form a 3- to 6 membered carbocyclic ring, which is unsubstituted or substituted one, two or three times by R10, R10 and R20 are the same or different and are independently of one another hydrogen atom, halogen, —($C_1$-$C_6$)-alkyl, —($C_0$-$C_4$)-alkyl-OH, —($C_1$-$C_3$)-fluoroalkyl, —($C_0$-$C_4$)-alkyl-O—($C_1$-$C_4$)-alkyl, —($C_0$-$C_5$)-alkyl-($C_3$-$C_8$)-cycloalkyl, —($C_0$-$C_2$)-alkylene-aryl, wherein aryl is as defined above and aryl is unsubstituted or substituted one, two or three times independent of each other by —($C_1$-$C_6$)-alkyl, halogen or —($C_3$-$C_8$)-cycloalkyl, or —($C_0$-$C_2$)-alkylene-heterocyclyl, wherein heterocyclyl is as defined above and heterocyclyl is unsubstituted or substituted one, two or three times independent of each other by —($C_1$-$C_6$)-alkyl, halogen or —($C_3$-$C_8$)-cycloalkyl, R12 is —($C_1$-$C_6$)-alkyl, —($C_1$-$C_6$)-alkyl-OH, —($C_1$-$C_6$)-alkyl-O—($C_1$-$C_6$)-alkyl, —($C_3$-$C_8$)-cycloalkyl, —($C_1$-$C_6$)-alkyl-O—($C_1$-$C_8$)-alkyl-($C_3$-$C_8$)-cycloalkyl, —($C_1$-$C_6$)-alkyl-($C_3$-$C_8$)-cycloalkyl, wherein said cycloalkyl ring is unsubstituted or substituted one, two or three times by —OH, —O—($C_1$-$C_4$)-alkyl or R10, R14 and R15 are the same or different and are independently of one another hydrogen atom or —($C_1$-$C_4$)-alkyl, R16 is hydrogen atom, —OH or —O—($C_1$-$C_4$)-alkyl, R21 and R22 are the same or different and are independently of one another
1) hydrogen atom,
2) —($C_1$-$C_6$)-alkyl, wherein alkyl is unsubstituted or mono-, di- or trisubstituted independently of one another by R7,
3) —($C_0$-$C_6$)-alkylene-($C_3$-$C_8$)-cycloalkyl,
4) —$SO_t$—R10, wherein t is 1 or 2,
5) —($C_0$-$C_6$)-alkylene-aryl, wherein aryl is as defined above and alkylene and aryl independently from one another are unsubstituted or mono-, di- or trisubstituted by R7,
6) —($C_1$-$C_3$)-fluoroalkyl,
7) —O—R12 or
8) —($C_0$-$C_6$)-alkylene-heterocyclyl, wherein heterocyclyl is as defined above and alkylene and heterocyclyl independently from one another are unsubstituted or mono-, di- or trisubstituted by R7, or R21 and R22 together with the nitrogen atom to which they are bonded form a 4- to 10-membered mono- or bicyclic heterocyclic ring which in addition to the nitrogen atom can contain one, two or three identical or different ring heteroatoms chosen from oxygen, sulfur and nitrogen, wherein said heterocyclic ring is unsubstituted or mono-, di- or trisubstituted independently of one another by R7, and R23 is hydrogen atom, —OH or —O—($C_1$-$C_4$)-alkyl,
in all its stereoisomeric forms and mixtures thereof in any ratio, and its physiologically tolerable salts.

2) Thus, the present invention also relates to compounds of the formula I, wherein

is a thiophenyl residue,

X is halogen, methyl or ethynyl,

R1 is —($C_0$-$C_3$)-alkylene-C(O)—R10, —($C_0$-$C_3$)-alkylene-C(O)—NH—R6, halogen, —($C_0$-$C_3$)-alkylene-C(O)—O—R10, —O—($C_1$-$C_4$)-alkyl, —O—($C_1$-$C_3$)-fluoroalkyl, —($C_0$-$C_4$)-alkylene-($C_1$-$C_3$)-fluoroalkyl, —($C_1$-$C_4$)-alkyl, wherein alkyl is unsubstituted or substituted one, two or three times by R8,
($C_0$-$C_5$)-alkylene-($C_3$-$C_8$)-cycloalkyl-R23, —($C_0$-$C_4$)-alkylene-aryl, wherein aryl is selected out of the group phenyl, naphthyl, biphenylyl, anthryl or fluorenyl, wherein aryl is mono-, di- or trisubstituted independently of one another by R8, or
—($C_0$-$C_4$)-alkylene-heterocyclyl, wherein heterocyclyl is selected out of the group acridinyl, azabenzimidazolyl, azaspirodecanyl, azepinyl, azetidinyl, aziridinyl, benzimidazolyl, 1,3-benzodioxolyl, benzofuranyl, benzothienyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phenylpyridyl, phthalazinyl, piperazinyl, piperidinyl, pteridinyl, purinyl, pyranyl, pyrazinyl, pyrazolidinyl, pyrazolinyl, pyrazolyl, pyridazinyl, pyridoimidazolyl, pyridooxazolyl, pyridopyrimidinyl, pyridothiazolyl, pyridothienyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinolyl, quinoxalinyl, quinuclidinyl, tetrahydrofuranyl, tetrahydroisoquinolinyl, tetrahydroquinolinyl, 1,4,5,6-tetrahydro-pyridazinyl, tetrahydropyranyl, tetrahydropyridinyl, tetrahydro-thiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,4-triazolyl, 1,2,5-triazolyl, 1,3,4-triazolyl and xanthenyl, and wherein said heterocyclyl is unsubstituted or mono-, di- or trisubstituted independently of one another by R8, R2 and R3 are independent of one another are identical or different and are a hydrogen atom, —($C_0$-$C_3$)-alkylene-C(O)—R10, —($C_0$-$C_3$)-alkylene-C(O)—NH—R6, —($C_0$-$C_3$)-alkylene-C(O)—O—R10, —O—($C_1$-$C_4$)-alkyl, —O—($C_1$-$C_3$)-fluoroalkyl, halogen, —($C_0$-$C_4$)-alkylene-($C_1$-$C_3$)-fluoroalkyl, —($C_0$-$C_5$)-alkylene-($C_3$-$C_8$)-cycloalkyl-R23,
—($C_1$-$C_4$)-alkyl, wherein alkyl is unsubstituted or substituted one, two or three times by R8,
—($C_0$-$C_4$)-alkylene-aryl, wherein aryl is as defined above and is mono-, di- or trisubstituted independently of one another by R8, or
—($C_0$-$C_4$)-alkylene-heterocyclyl, wherein heterocyclyl is as defined above and is unsubstituted or mono-, di- or trisubstituted independently of one another by R8, R4 and R5 are the same or different and are independently of one another
1) hydrogen atom,
2) —($C_1$-$C_6$)-alkyl, wherein alkyl is unsubstituted or mono-, di- or trisubstituted independently of one another by R7,
3) —($C_0$-$C_6$)-alkylene-($C_3$-$C_8$)-cycloalkyl,
4) —$SO_t$—R10, wherein t is 1 or 2,
5) —($C_0$-$C_6$)-alkylene-aryl, wherein aryl is as defined above and alkylene and aryl independently from one another are unsubstituted or mono-, di- or trisubstituted by R7,
6) —($C_1$-$C_3$)-fluoroalkyl, 7) —O—($C_1$-$C_4$)-alkyl or
8) —($C_0$-$C_6$)-alkylene-heterocyclyl, wherein heterocyclyl is as defined above and alkylene and heterocyclyl independently from one another are unsubstituted or mono-, di- or trisubstituted by R7,
provided that R4 and R5 are not each a hydrogen atom, or
R4 and R5 together with the nitrogen atom to which they are bonded form a 4- to 10-membered mono- or bicyclic heterocyclic ring which in addition to the nitrogen atom can contain one, two or three identical or different ring heteroatoms chosen from oxygen, sulfur and nitrogen, wherein said heterocyclic ring is unsubstituted or mono-, di- or trisubstituted independently of one another by R7,
R6 is 1) heterocyclyl, wherein heterocyclyl is as defined above and is un-substituted or mono-, di- or tri substituted independently of one another by R8 or 2) aryl, which is as defined above wherein aryl is unsubstituted or mono-, di- or trisubstituted independently of one another by R8,
R7 is halogen, —$NO_2$, =O, —$CF_3$, —($C_0$-$C_3$)-alkylene-C(O)—O—R10, —C(O)—R10, —CN, —OH, —$NH_2$, —C(O)—N(R10)-R20, —N(R10)-R20, =$F_2$, —O—($C_1$-$C_3$)-fluoroalkyl, —($C_0$-$C_4$)-alkylene-($C_1$-$C_3$)-fluoroalkyl, —($C_0$-$C_3$)-alkylene-($C_3$-$C_8$)-cycloalkyl, —($C_1$-$C_8$)-alkyl, wherein alkyl is unsubstituted or mono-, di- or trisubstituted independently of one another by halogen, $NH_2$, —OH or —O—($C_1$-$C_6$)-alkyl, —O—($C_1$-$C_6$)-alkyl, wherein alkyl is unsubstituted or mono-, di- or trisubstituted independently of one another by halogen, $NH_2$, —OH or a methoxy residue, or —($C_0$-$C_3$)-alkylene-heterocyclyl, wherein heterocyclyl is as defined above and is unsubstituted mono-, di- or trisubstituted independently of one another by R10,
R8 is halogen, —$NO_2$, —CN, =O, —OH, —$CF_3$, —C(O)—O—R10, —($C_3$-$C_8$)-cycloalkyl, —($C_0$-$C_3$)-alkylene-O—R10, —Si—$(CH_3)_3$, —N(R10)-S(O)$_u$—R10, wherein u is 1 or 2, —S—R10, —$SO_r$—R10, wherein r is 1 or 2, —S(O)$_v$—N(R10)-R20, wherein v is 1 or 2, —C(O)—R10, —($C_1$-$C_8$)-alkyl, —($C_1$-$C_8$)-alkoxy, phenyl, phenyloxy-, —O—R9, —($C_1$-$C_3$)-fluoroalkyl, —($C_0$-$C_4$)-alkyl-C(O)—O—C(R9, R11)-O—C(O)—R12, —NH—C(O)—NH—R10, —NH—C(O)—NH—R6, —O—$CF_3$, —NH—C(O)—O—R10, or —($C_0$-$C_4$)-alkyl-C(O)—O—C(R9, R11)-O—C(O)—O—R12,
R9 and R11 are the same or different and are independently of one another hydrogen, —($C_1$-$C_6$)-alkyl, or together with the carbon atom to which they are bonded form a 3- to 6 membered carbocyclic ring, which is unsubstituted or substituted one, two or three times by R10,
R10 and R20 are the same or different and are independently of one another hydrogen atom, halogen, —($C_1$-$C_6$)-alkyl, —($C_0$-$C_4$)-alkyl-OH, —($C_1$-$C_3$)-fluoroalkyl, —($C_0$-$C_4$)-alkyl-O—($C_1$-$C_4$)-alkyl, —($C_0$-$C_5$)-alkyl-($C_3$-$C_8$)-cycloalkyl, —($C_0$-$C_2$)-alkylene-aryl, wherein aryl is as defined above and aryl is unsubstituted or substituted one, two or three times independent of each other by —($C_1$-$C_6$)-alkyl, halogen or —($C_3$-$C_8$)-cycloalkyl, or —($C_0$-$C_2$)-alkylene-heterocyclyl, wherein heterocyclyl is as defined above and heterocyclyl is unsubstituted or substituted one, two or three times independent of each other by —($C_1$-$C_6$)-alkyl, halogen or —($C_3$-$C_8$)-cycloalkyl,
R12 is —($C_1$-$C_6$)-alkyl, —($C_1$-$C_6$)-alkyl-OH, —($C_1$-$C_6$)-alkyl-O—($C_1$-$C_6$)-alkyl, —($C_3$-$C_8$)-cycloalkyl, —($C_1$-$C_6$)-alkyl-O—($C_1$-$C_8$)-alkyl-($C_3$-$C_8$)-cycloalkyl, —($C_1$-$C_6$)-alkyl-($C_3$-$C_8$)-cycloalkyl, wherein said cycloalkyl ring is unsubstituted or substituted one, two or three times by —OH, —O—($C_1$-$C_4$)-alkyl or R10,
R16 is hydrogen atom, —OH or —O—($C_1$-$C_4$)-alkyl, and
R23 is hydrogen atom, —OH or —O—($C_1$-$C_4$)-alkyl,
in all its stereoisomeric forms and mixtures thereof in any ratio, and its physiologically tolerable salts.
3) Thus, the present invention also relates to compounds of the formula I, wherein

is a thiophenyl residue,
X is halogen, methyl or ethynyl,
R1 is —($C_0$-$C_3$)-alkylene-C(O)—R10, —($C_0$-$C_3$)-alkylene-C(O)—NH—R6, halogen, —($C_0$-$C_3$)-alkylene-C(O)—O—R10, —O—($C_1$-$C_4$)-alkyl, —O—($C_1$-$C_3$)-fluoroalkyl, —($C_0$-$C_4$)-alkylene-($C_1$-$C_3$)-fluoroalkyl or —($C_1$-$C_4$)-alkyl, wherein alkyl is unsubstituted or substituted one, two or three times by R8,
R2 is —($C_0$-$C_3$)-alkylene-C(O)—R10, —($C_0$-$C_3$)-alkylene-C(O)—NH—R6, halogen, —($C_0$-$C_3$)-alkylene-C(O)—O—R10, —O—($C_1$-$C_4$)-alkyl, —O—($C_1$-$C_3$)-fluoroalkyl, —($C_0$-$C_4$)-alkylene-($C_1$-$C_3$)-fluoroalkyl or —($C_1$-$C_4$)-alkyl, wherein alkyl is unsubstituted or substituted one, two or three times by R8,
($C_0$-$C_5$)-alkylene-($C_3$-$C_8$)-cycloalkyl-R23, —($C_0$-$C_4$)-alkylene-aryl, wherein aryl is selected out of the group phenyl, naphthyl, biphenylyl, anthryl or fluorenyl, wherein aryl is mono-, di- or trisubstituted independently of one another by R8, or
—($C_0$-$C_4$)-alkylene-heterocyclyl, wherein heterocyclyl is selected out of the group acridinyl, azabenzimidazolyl, azaspirodecanyl, azepinyl, azetidinyl, aziridinyl, benzimidazolyl, 1,3-benzodioxolyl, benzofuranyl, benzothienyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phenylpyridyl, phthalazinyl, piperazinyl, piperidinyl, pteridinyl, purinyl, pyranyl, pyrazinyl, pyrazolidinyl, pyrazolinyl, pyrazolyl, pyridazinyl, pyridoimidazolyl, pyridooxazolyl, pyridopyrimidinyl, pyridothiazolyl, pyridothienyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinolyl, quinoxalinyl, quinuclidinyl, tetrahydrofuranyl, tetrahydroisoquinolinyl, tetrahydroquinolinyl, 1,4,5,6-tetrahydro-pyridazinyl, tetrahydropyranyl, tetrahydropyridinyl, tetrahydro-thiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,4-triazolyl, 1,2,5-triazolyl, 1,3,4-triazolyl and xanthenyl, and wherein said heterocyclyl is unsubstituted or mono-, di- or trisubstituted independently of one another by R8, R3 is a hydrogen atom, —(C$_0$-C$_3$)-alkylene-C(O)—R10, —(C$_0$-C$_3$)-alkylene-C(O)—NH—R6, —(C$_0$-C$_3$)-alkylene-C(O)—O—R10, —O—(C$_1$-C$_4$)-alkyl, —O—(C$_1$-C$_3$)-fluoroalkyl, halogen, —(C$_0$-C$_4$)-alkylene-(C$_1$-C$_3$)-fluoroalkyl, —(C$_0$-C$_5$)-alkylene-(C$_3$-C$_8$)-cycloalkyl-R23, or —(C$_1$-C$_4$)-alkyl, wherein alkyl is unsubstituted or substituted one, two or three times by R8, R4 and R5 are the same or different and are independently of one another
1) hydrogen atom,
2) —(C$_1$-C$_6$)-alkyl, wherein alkyl is unsubstituted or mono-, di- or trisubstituted independently of one another by R7,
3) —(C$_0$-C$_6$)-alkylene-(C$_3$-C$_8$)-cycloalkyl,
4) —SO$_t$—R10, wherein t is 1 or 2,
5) —(C$_0$-C$_6$)-alkylene-aryl, wherein aryl is as defined above and alkylene and aryl independently from one another are unsubstituted or mono-, di- or trisubstituted by R7,
6) —(C$_1$-C$_3$)-fluoroalkyl,
7) —O—(C$_1$-C$_4$)-alkyl or
8) —(C$_0$-C$_6$)-alkylene-heterocyclyl, wherein heterocyclyl is as defined above and alkylene and heterocyclyl independently from one another are unsubstituted or mono-, di- or trisubstituted by R7, provided that R4 and R5 are not each a hydrogen atom, or R4 and R5 together with the nitrogen atom to which they are bonded form a 4- to 10-membered mono- or bicyclic heterocyclic ring, which is selected from 2-oxa-5-aza-bicyclo[2.2.1]heptane, azepane, azepine, azetidine, 2,5-diaza-bicyclo[2.2.1]heptane, 1,4-diazepane, 1,2-diazepine, 1,3-diazepine, 1,4-diazepine, 2,3-dihydro-1H-isoindole, 2,3-dihydro-1H-pyrrolo[3,4-c]pyridine, 6,7-dihydro-5H-pyrrolo[3,4-b]pyridine, 5,6-dihydro-4H-pyrrolo[3,4-d]thiazole, dioxazole, dioxazine, imidazole, imidazoline, imidazolidine, isothiazole, isothiazolidine, isothiazoline, isoxazole, isoxazoline, isoxazolidine, 2-isoxazoline, morpholine, octahydro-pyrido[1,2-a]pyrazine, octahydro-pyrrolo[3,4-b]pyridine, octahydro-pyrrolo[1,2-a]pyrazine, [1,4]oxazepane, 1,4-oxazepine, oxazole, piperazine, piperidine, piperidinone, pyrazine, pyrazole, pyrazoline, pyrazolidine, pyridazine, pyridine, pyridone, pyrimidine, pyrrole, pyrrolidine, pyrrolidinone, pyrroline, 4,5,6,7-tetrahydro-1H-imidazo[4,3-c]pyridine, tetrahydropyridine, 1,4,5,6-tetrahydro-pyrrolo[3,4-c]pyrazole, 4,5,6,7-tetrahydro-thiazolo[5,4-c]pyridine, 5,6,7,8-tetrahydro-[1,2,4]triazolo[4,3-a]pyrazine, 4,5,6,7-tetrahydro-thieno[3,2-c]pyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole or 1,2,4-triazole, wherein said heterocyclic ring is unsubstituted or mono-, di- or trisubstituted independently of one another by R7, R6 is 1) heterocyclyl, wherein heterocyclyl is as defined above and is un-substituted or mono-, di- or tri substituted independently of one another by R8 or 2) aryl, which is as defined above wherein aryl is unsubstituted or mono-, di- or trisubstituted independently of one another by R8, R7 is halogen, —NO$_2$, =O, —CF$_3$, —(C$_0$-C$_3$)-alkylene-C(O)—O—R10, —C(O)—R10, —CN, —OH, —NH$_2$, —C(O)—N(R10)-R20, —N(R10)-R20, =F$_2$, —O—(C$_1$-C$_3$)-fluoroalkyl, —(C$_0$-C$_4$)-alkylene-(C$_1$-C$_3$)-fluoroalkyl, —(C$_0$-C$_3$)-alkylene-(C$_3$-C$_8$)-cycloalkyl, —(C$_1$-C$_8$)-alkyl, wherein alkyl is unsubstituted or mono-, di- or trisubstituted independently of one another by halogen, NH$_2$, —OH or —O—(C$_1$-C$_6$)-alkyl, —O—(C$_1$-C$_6$)-alkyl, wherein alkyl is unsubstituted or mono-, di- or trisubstituted independently of one another by halogen, NH$_2$, —OH or a methoxy residue, or —(C$_0$-C$_3$)-alkylene-heterocyclyl, wherein heterocyclyl is as defined above and is unsubstituted mono-, di- or trisubstituted independently of one another by R10, R8 is halogen, —NO$_2$, —CN, =O, —OH, —CF$_3$, —C(O)—O—R10, —(C$_3$-C$_8$)-cycloalkyl, —(C$_0$-C$_3$)-alkylene-O—R10, —Si—(CH$_3$)$_3$, —N(R10)-S(O)$_u$—R10, wherein u is 1 or 2, —S—R10, —SO$_r$—R10, wherein r is 1 or 2, —S(O)$_v$, —N(R10)-R20, wherein v is 1 or 2, —C(O)—R10, —(C$_1$-C$_8$)-alkyl, —(C$_1$-C$_8$)-alkoxy, phenyl, phenyloxy-, —O—CF$_3$, —(C$_1$-C$_3$)-fluoroalkyl, —NH—C(O)—NH—R6 or —NH—C(O)—O—R10, R10 and R20 are the same or different and are independently of one another hydrogen atom, halogen, —(C$_1$-C$_6$)-alkyl, —(C$_0$-C$_4$)-alkyl-OH, —(C$_1$-C$_3$)-fluoroalkyl, —(C$_0$-C$_4$)-alkyl-O—(C$_1$-C$_4$)-alkyl, —(C$_0$-C$_5$)-alkyl-(C$_3$-C$_8$)-cycloalkyl, —(C$_0$-C$_2$)-alkylene-aryl, wherein aryl is as defined above and aryl is unsubstituted or substituted one, two or three times independent of each other by —(C$_1$-C$_6$)-alkyl, halogen or —(C$_3$-C$_8$)-cycloalkyl, or —(C$_0$-C$_2$)-alkylene-heterocyclyl, wherein heterocyclyl is as defined above and heterocyclyl is unsubstituted or substituted one, two or three times independent of each other by —(C$_1$-C$_6$)-alkyl, halogen or —(C$_3$-C$_8$)-cycloalkyl, R16 is hydrogen atom, —OH or —O—(C$_1$-C$_4$)-alkyl, and R23 is hydrogen atom, —OH or —O—(C$_1$-C$_4$)-alkyl, in all its stereoisomeric forms and mixtures thereof in any ratio, and its physiologically tolerable salts.

4) The present invention also relates to compounds of the formula Ia,

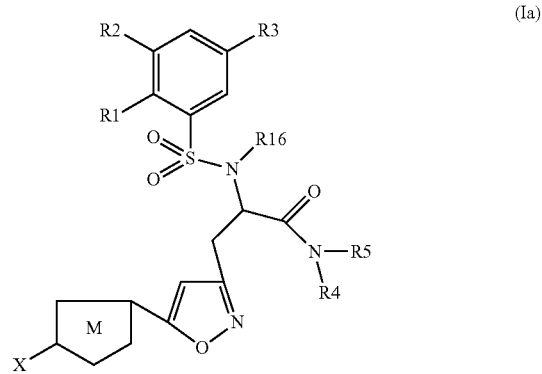

(Ia)

wherein

is a thiophenyl residue,

X is halogen, methyl or ethynyl,

R1 is —($C_0$-$C_3$)-alkylene-C(O)—R10, —($C_0$-$C_3$)-alkylene-C(O)—NH—R6, halogen, —($C_0$-$C_3$)-alkylene-C(O)—O—R10, —O—($C_1$-$C_4$)-alkyl, —O—($C_1$-$C_3$)-fluoroalkyl, —($C_0$-$C_4$)-alkylene-($C_1$-$C_3$)-fluoroalkyl or —($C_1$-$C_4$)-alkyl, wherein alkyl is unsubstituted or substituted one, two or three times by R8, R2 is —($C_0$-$C_3$)-alkylene-C(O)—R10, —($C_0$-$C_3$)-alkylene-C(O)—NH—R6, halogen, —($C_0$-$C_3$)-alkylene-C(O)—O—R10, —O—($C_1$-$C_4$)-alkyl, —O—($C_1$-$C_3$)-fluoroalkyl, —($C_0$-$C_4$)-alkylene-($C_1$-$C_3$)-fluoroalkyl or —($C_1$-$C_4$)-alkyl, wherein alkyl is unsubstituted or substituted one, two or three times by R8,
—($C_0$-$C_5$)-alkylene-($C_3$-$C_8$)-cycloalkyl-R23, —($C_0$-$C_4$)-alkylene-aryl, wherein aryl is selected out of the group phenyl, naphthyl, biphenylyl, anthryl or fluorenyl, wherein aryl is mono-, di- or trisubstituted independently of one another by R8, or
—($C_0$-$C_4$)-alkylene-heterocyclyl, wherein heterocyclyl is selected out of the group acridinyl, azabenzimidazolyl, azaspirodecanyl, azepinyl, azetidinyl, aziridinyl, benzimidazolyl, 1,3-benzodioxolyl, benzofuranyl, benzothienyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phenylpyridyl, phthalazinyl, piperazinyl, piperidinyl, pteridinyl, purinyl, pyranyl, pyrazinyl, pyrazolidinyl, pyrazolinyl, pyrazolyl, pyridazinyl, pyridoimidazolyl, pyridooxazolyl, pyridopyrimidinyl, pyridothiazolyl, pyridothienyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinolyl, quinoxalinyl, quinuclidinyl, tetrahydrofuranyl, tetrahydroisoquinolinyl, tetrahydroquinolinyl, 1,4,5,6-tetrahydro-pyridazinyl, tetrahydropyranyl, tetrahydropyridinyl, tetrahydro-thiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazinyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,4-triazolyl, 1,2,5-triazolyl, 1,3,4-triazolyl and xanthenyl, and wherein said heterocyclyl is unsubstituted or mono-, di- or trisubstituted independently of one another by R8, R3 is a hydrogen atom, —($C_0$-$C_3$)-alkylene-C(O)—R10, —($C_0$-$C_3$)-alkylene-C(O)—NH—R6, —($C_0$-$C_3$)-alkylene-C(O)—O—R10, —O—($C_1$-$C_4$)-alkyl, —O—($C_1$-$C_3$)-fluoroalkyl, halogen, —($C_0$-$C_4$)-alkylene-($C_1$-$C_3$)-fluoroalkyl, —($C_0$-$C_5$)-alkylene-($C_3$-$C_8$)-cycloalkyl-R23, or —($C_1$-$C_4$)-alkyl, wherein alkyl is unsubstituted or substituted one, two or three times by R8, R4 and R5 are the same or different and are independently of one another
1) hydrogen atom,
2) —($C_1$-$C_6$)-alkyl, wherein alkyl is unsubstituted or mono-, di- or trisubstituted independently of one another by R7,
3) —($C_0$-$C_6$)-alkylene-($C_3$-$C_8$)-cycloalkyl,
4) —$SO_t$—R10, wherein t is 1 or 2,
5) —($C_0$-$C_6$)-alkylene-aryl, wherein aryl is as defined above and alkylene and aryl independently from one another are unsubstituted or mono-, di- or trisubstituted by R7,
6) —($C_1$-$C_3$)-fluoroalkyl,
7) —O—($C_1$-$C_4$)-alkyl or
8) —($C_0$-$C_6$)-alkylene-heterocyclyl, wherein heterocyclyl is as defined above and alkylene and heterocyclyl independently from one another are unsubstituted or mono-, di- or trisubstituted by R7,
provided that R4 and R5 are not each a hydrogen atom, or R4 and R5 together with the nitrogen atom to which they are bonded form a 4- to 10-membered mono- or bicyclic heterocyclic ring, which is selected from 2-oxa-5-aza-bicyclo[2.2.1]heptane, azepane, azepine, azetidine, 2,5-diaza-bicyclo[2.2.1]heptane, 1,4-diazepane, 1,2-diazepine, 1,3-diazepine, 1,4-diazepine, 2,3-dihydro-1H-isoindole, 2,3-dihydro-1H-pyrrolo[3,4-c]pyridine, 6,7-dihydro-5H-pyrrolo[3,4-b]pyridine, 5,6-dihydro-4H-pyrrolo[3,4-d]thiazole, dioxazole, dioxazine, imidazole, imidazoline, imidazolidine, isothiazole, isothiazolidine, isothiazoline, isoxazole, isoxazoline, isoxazolidine, 2-isoxazoline, morpholine, octahydro-pyrido[1,2-a]pyrazine, octahydro-pyrrolo[3,4-b]pyridine, octahydro-pyrrolo[1,2-a]pyrazine, [1,4]oxazepane, 1,4-oxazepine, oxazole, piperazine, piperidine, piperidinone, pyrazine, pyrazole, pyrazoline, pyrazolidine, pyridazine, pyridine, pyridone, pyrimidine, pyrrole, pyrrolidine, pyrrolidinone, pyrroline, 4,5,6,7-tetrahydro-1H-imidazo[4,3-c]pyridine, tetrahydropyridine, 1,4,5,6-tetrahydro-pyrrolo[3,4-c]pyrazole, 4,5,6,7-tetrahydro-thiazolo[5,4-c]pyridine, 5,6,7,8-tetrahydro-[1,2,4]triazolo[4,3-a]pyrazine, 4,5,6,7-tetrahydro-thieno[3,2-c]pyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole or 1,2,4-triazole, wherein said heterocyclic ring is unsubstituted or mono-, di- or trisubstituted independently of one another by R7, R6 is 1) heterocyclyl, wherein heterocyclyl is as defined above and is un-substituted or mono-, di- or tri substituted independently of one another by R8 or 2) aryl, which is as defined above wherein aryl is unsubstituted or mono-, di- or trisubstituted independently of one another by R8, R7 is halogen, —$NO_2$, =O, —$CF_3$, —($C_0$-$C_3$)-alkylene-C(O)—O—R10, —C(O)—R10, —CN, —OH, —$NH_2$, —C(O)—N(R10)-R20, —N(R10)-R20, =$F_2$, —O—($C_1$-$C_3$)-fluoroalkyl, —($C_0$-$C_4$)-alkylene-($C_1$-$C_3$)-fluoroalkyl, —($C_0$-$C_3$)-alkylene-($C_3$-$C_8$)-cycloalkyl, —($C_1$-$C_8$)-alkyl, wherein alkyl is unsubstituted or mono-, di- or trisubstituted independently of one another by halogen, $NH_2$, —OH or —O—$(C_1$-$C_6)$-alkyl, —O—$(C_1$-$C_6)$-alkyl, wherein alkyl is unsubstituted or mono-, di- or trisubstituted independently of one another by halogen, $NH_2$, —OH or a methoxy residue, or —$(C_0$-$C_3)$-alkylene-heterocyclyl, wherein heterocyclyl is as defined above and is unsubstituted mono-, di- or trisubstituted independently of one another by R10, R8 is halogen, —$NO_2$, —CN, =O, —OH, —$CF_3$, —C(O)—O—R10, —$(C_3$-$C_8)$-cycloalkyl, —$(C_0$-$C_3)$-alkylene-O—R10, —Si—$(CH_3)_3$, —N(R10)-S(O)$_u$—R10, wherein u is 1 or 2, —S—R10, —SO$_r$—R10, wherein r is 1 or 2, —S(O)$_v$—N(R10)-R20, wherein v is 1 or 2, —C(O)—R10, —$(C_1$-$C_8)$-alkyl, —$(C_1$-$C_8)$-alkoxy, phenyl, phenyloxy-, —O—$CF_3$, —$(C_1$-$C_3)$-fluoroalkyl, —NH—C(O)—NH—R6 or —NH—C(O)—O—R10, R10 and R20 are the same or different and are independently of one another hydrogen atom, halogen, —$(C_1$-$C_6)$-alkyl, —$(C_0$-$C_4)$-alkyl-OH, —$(C_1$-$C_3)$-fluoroalkyl, —$(C_0$-$C_4)$-alkyl-O—$(C_1$-$C_4)$-alkyl, —$(C_0$-$C_5)$-alkyl-$(C_3$-$C_8)$-cycloalkyl, —$(C_0$-$C_2)$-alkylene-aryl, wherein aryl is as defined above and aryl is unsubstituted or substituted one, two or three times independent of each other by —$(C_1$-$C_6)$-alkyl, halogen or —$(C_3$-$C_8)$-cycloalkyl, or —$(C_0$-$C_2)$-alkylene-heterocyclyl, wherein heterocyclyl is as defined above and heterocyclyl is unsubstituted or substituted one, two or three times independent of each other by —$(C_1$-$C_6)$-alkyl, halogen or —$(C_3$-$C_8)$-cycloalkyl, R16 is hydrogen atom, —OH or —O—$(C_1$-$C_4)$-alkyl, and
R23 is hydrogen atom, —OH or —O—$(C_1$-$C_4)$-alkyl,
in all its stereoisomeric forms and mixtures thereof in any ratio, and its physiologically tolerable salts.

5) The present invention also relates to compounds of the formula Ia, wherein

is a thiophenyl residue,

X is halogen, methyl or ethynyl,

R1 is —$(C_0$-$C_3)$-alkylene-C(O)—R10, halogen, —$(C_0$-$C_3)$-alkylene-C(O)—O—R10, —O—$(C_1$-$C_4)$-alkyl, —O—$(C_1$-$C_3)$-fluoroalkyl, —$(C_0$-$C_4)$-alkylene-$(C_1$-$C_3)$-fluoroalkyl or —$(C_1$-$C_4)$-alkyl, wherein alkyl is unsubstituted or substituted one, two or three times by R8, R2 is —$(C_0$-$C_3)$-alkylene-C(O)—R10, halogen, —$(C_0$-$C_3)$-alkylene-C(O)—O—R10, —O—$(C_1$-$C_4)$-alkyl, —O—$(C_1$-$C_3)$-fluoroalkyl, —$(C_0$-$C_4)$-alkylene-$(C_1$-$C_3)$-fluoroalkyl, —$(C_1$-$C_4)$-alkyl, wherein alkyl is unsubstituted or substituted one, two or three times by R8, —$(C_0$-$C_4)$-alkylene-aryl, wherein aryl is selected out of the group phenyl, naphthyl, biphenylyl, anthryl or fluorenyl, wherein aryl is mono-, di- or trisubstituted independently of one another by R8, or
—$(C_0$-$C_4)$-alkylene-heterocyclyl, wherein heterocyclyl is selected out of the group morpholinyl, oxadiazolyl, 1,2,4-oxadiazolyl, 1,3,4-oxadiazolyl, 1,4-oxazepanyl, piperidinyl, pyrazolyl, pyridyl, pyrrolidinyl or thiazolyl, and wherein said heterocyclyl is unsubstituted or mono-, di- or trisubstituted independently of one another by R8, R3 is a hydrogen atom, —$(C_0$-$C_3)$-alkylene-C(O)—R10, —$(C_0$-$C_3)$-alkylene-C(O)—O—R10, —O—$(C_1$-$C_4)$-alkyl, —O—$(C_1$-$C_3)$-fluoroalkyl, halogen, —$(C_0$-$C_4)$-alkylene-$(C_1$-$C_3)$-fluoroalkyl or —$(C_1$-$C_4)$-alkyl, wherein alkyl is unsubstituted or substituted one, two or three times by R8, R4 and R5 are the same or different and are independently of one another
1) hydrogen atom,
2) —$(C_1$-$C_6)$-alkyl, wherein alkyl is unsubstituted or mono-, di- or trisubstituted independently of one another by R7,
3) —$(C_0$-$C_6)$-alkylene-$(C_3$-$C_8)$-cycloalkyl,
4) —SO$_t$—R10, wherein t is 1 or 2,
5) —$(C_0$-$C_6)$-alkylene-aryl, wherein aryl is as defined above and alkylene and aryl independently from one another are unsubstituted or mono-, di- or trisubstituted by R7,
6) —$(C_1$-$C_3)$-fluoroalkyl,
7) —O—$(C_1$-$C_4)$-alkyl or
8) —$(C_0$-$C_6)$-alkylene-heterocyclyl, wherein heterocyclyl is as defined above and alkylene and heterocyclyl independently from one another are unsubstituted or mono-, di- or trisubstituted by R7, provided that R4 and R5 are not each a hydrogen atom, or R4 and R5 together with the nitrogen atom to which they are bonded form a 4- to 10-membered mono- or bicyclic heterocyclic ring, which is selected from 2-oxa-5-aza-bicyclo[2.2.1]heptane, azepane, azepine, azetidine, 2,5-diaza-bicyclo[2.2.1]heptane, 1,4-diazepane, 1,2-diazepine, 1,3-diazepine, 1,4-diazepine, 2,3-dihydro-1H-isoindole, 2,3-dihydro-1H-pyrrolo[3,4-c]pyridine, 6,7-dihydro-5H-pyrrolo[3,4-b]pyridine, 5,6-dihydro-4H-pyrrolo[3,4-d]thiazole, dioxazole, dioxazine, imidazole, imidazoline, imidazolidine, isothiazole, isothiazolidine, isothiazoline, isoxazole, isoxazoline, isoxazolidine, 2-isoxazoline, morpholine, octahydro-pyrido[1,2-a]pyrazine, octahydro-pyrrolo[3,4-b]pyridine, octahydro-pyrrolo[1,2-a]pyrazine, [1,4]oxazepane, 1,4-oxazepine, oxazole, piperazine, piperidine, piperidinone, pyrazine, pyrazole, pyrazoline, pyrazolidine, pyridazine, pyridine, pyridone, pyrimidine, pyrrole, pyrrolidine, pyrrolidinone, pyrroline, 4,5,6,7-tetrahydro-1H-imidazo[4,3-c]pyridine, tetrahydropyridine, 1,4,5,6-tetrahydro-pyrrolo[3,4-c]pyrazole, 4,5,6,7-tetrahydro-thiazolo[5,4-c]pyridine, 5,6,7,8-tetrahydro-[1,2,4]triazolo[4,3-a]pyrazine, 4,5,6,7-tetrahydro-thieno[3,2-c]pyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole or 1,2,4-triazole, wherein said heterocyclic ring is unsubstituted or mono-, di- or trisubstituted independently of one another by R7, R7 is halogen, —$NO_2$, =O, —$CF_3$, —$(C_0$-$C_3)$-alkylene-C(O)—O—R10, —C(O)—R10, —CN, —OH, —$NH_2$, —C(O)—N(R10)-R20, —N(R10)-R20, =$F_2$, —O—$(C_1$-$C_3)$-fluoroalkyl, —$(C_0$-$C_4)$-alkylene-$(C_1$-$C_3)$-fluoroalkyl, —$(C_0$-$C_3)$-alkylene-$(C_3$-$C_8)$-cycloalkyl, —$(C_1$-$C_8)$-alkyl, wherein alkyl is unsubstituted or mono-, di- or trisubstituted independently of one another by halogen, $NH_2$, —OH or —O—$(C_1$-$C_6)$-alkyl, —O—$(C_1$-$C_6)$-alkyl, wherein alkyl is unsubstituted or mono-, di- or trisubstituted independently of one another by halogen, $NH_2$, —OH or a methoxy residue, or —$(C_0$-$C_3)$-alkylene-heterocyclyl, wherein heterocyclyl is as defined above and is unsubstituted mono-, di- or trisubstituted independently of one another by R10, R8 is halogen, —$NO_2$, —CN, =O, —OH, —$CF_3$, —C(O)—O—R10, —$(C_3$-$C_8)$-cycloalkyl, —$(C_0$-$C_3)$-alkylene-O—R10, —Si—$(CH_3)_3$, —N(R10)-S(O)$_u$—R10, wherein u is 1 or 2, —S—R10, —SO$_r$—R10, wherein r is 1 or 2, —S(O)$_v$—N(R10)-R20, wherein v is 1 or 2, —C(O)—R10, —(C$_1$-C$_8$)-alkyl, —(C$_1$-C$_8$)-alkoxy, phenyl, phenyloxy-, —O—CF$_3$, —(C$_1$-C$_3$)-fluoroalkyl or —NH—C(O)—O—R10, R10 and R20 are the same or different and are independently of one another hydrogen atom, halogen, —(C$_1$-C$_6$)-alkyl, —(C$_0$-C$_4$)-alkyl-OH, —(C$_1$-C$_3$)-fluoroalkyl, —(C$_0$-C$_4$)-alkyl-O—(C$_1$-C$_4$)-alkyl, (C$_0$-C$_5$)-alkyl-(C$_3$-C$_8$)-cycloalkyl, —(C$_0$-C$_2$)-alkylene-aryl, wherein aryl is as defined above and aryl is unsubstituted or substituted one, two or three times independent of each other by —(C$_1$-C$_6$)-alkyl, halogen or —(C$_3$-C$_8$)-cycloalkyl, or —(C$_0$-C$_2$)-alkylene-heterocyclyl, wherein heterocyclyl is as defined above and heterocyclyl is unsubstituted or substituted one, two or three times independent of each other by —(C$_1$-C$_6$)-alkyl, halogen or —(C$_3$-C$_8$)-cycloalkyl, R16 is hydrogen atom, —OH or —O—(C$_1$-C$_4$)-alkyl, and R23 is hydrogen atom, —OH or —O—(C$_1$-C$_4$)-alkyl, in all its stereoisomeric forms and mixtures thereof in any ratio, and its physiologically tolerable salts.

6) Thus, the present invention also relates to compounds of the formula Ia, wherein

is a thiophenyl residue,

X is halogen,

R1 is —O—(C$_1$-C$_4$)-alkyl, —O—(C$_1$-C$_3$)-fluoroalkyl, halogen or —(C$_1$-C$_4$)-alkyl, R2 is halogen or —(C$_0$-C$_4$)-alkylene-heterocyclyl, wherein heterocyclyl is selected out of the group morpholinyl, oxadiazolyl, 1,2,4-oxadiazolyl, 1,3,4-oxadiazolyl, 1,4-oxazepanyl, piperidinyl, pyrazolyl, pyridyl, pyrrolidinyl or thiazolyl, and wherein said heterocyclyl is unsubstituted or mono-, di- or trisubstituted independently of one another by R8, R3 is a hydrogen atom, halogen or —(C$_1$-C$_4$)-alkyl, R4 and R5 are the same or different and are independently of one another hydrogen atom or —(C$_0$-C$_4$)-alkylene-(C$_3$-C$_6$)-cycloalkyl,
provided that R4 and R5 are not each a hydrogen atom, or R4 and R5 together with the nitrogen atom to which they are bonded form a 4- to 10-membered mono- or bicyclic heterocyclic ring, which is selected from 2-oxa-5-aza-bicyclo[2.2.1]heptane, azepane, azepine, azetidine, 2,5-diaza-bicyclo[2.2.1]heptane, 1,4-diazepane, 1,2-diazepine, 1,3-diazepine, 1,4-diazepine, 2,3-dihydro-1H-isoindole, 2,3-dihydro-1H-pyrrolo[3,4-c]pyridine, 6,7-dihydro-5H-pyrrolo[3,4-b]pyridine, 5,6-dihydro-4H-pyrrolo[3,4-d]thiazole, dioxazole, dioxazine, imidazole, imidazoline, imidazolidine, isothiazole, isothiazolidine, isothiazoline, isoxazole, isoxazoline, isoxazolidine, 2-isoxazoline, morpholine, octahydro-pyrido[1,2-a]pyrazine, octahydro-pyrrolo[3,4-b]pyridine, octahydro-pyrrolo[1,2-a]pyrazine, [1,4]oxazepane, 1,4-oxazepine, oxazole, piperazine, piperidine, piperidinone, pyrazine, pyrazole, pyrazoline, pyrazolidine, pyridazine, pyridine, pyridone, pyrimidine, pyrrole, pyrrolidine, pyrrolidinone, pyrroline, 4,5,6,7-tetrahydro-1H-imidazo[4,3-c]pyridine, tetrahydropyridine, 1,4,5,6-tetrahydro-pyrrolo[3,4-c]pyrazole, 4,5,6,7-tetrahydro-thiazolo[5,4-c]pyridine, 5,6,7,8-tetrahydro-[1,2,4]triazolo[4,3-a]pyrazine, 4,5,6,7-tetrahydro-thieno[3,2-c]pyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole or 1,2,4-triazole, wherein said heterocyclic ring is unsubstituted or mono-, di- or trisubstituted independently of one another by R7, R7 is halogen, =O, —(C$_0$-C$_3$)-alkylene-C(O)—O—R10, —C(O)—R10, —OH, —NH$_2$, =F$_2$, —O—(C$_1$-C$_3$)-fluoroalkyl, —(C$_0$-C$_3$)-alkylene-(C$_1$-C$_3$)-fluoroalkyl, —(C$_1$-C$_6$)-alkyl, wherein alkyl is unsubstituted or mono-, di- or trisubstituted independently of one another by halogen, NH$_2$, —OH or —O—(C$_1$-C$_6$)-alkyl, —(C$_0$-C$_3$)-alkylene-(C$_3$-C$_8$)-cycloalkyl or —O—(C$_1$-C$_6$)-alkyl, wherein alkyl is unsubstituted or mono-, di- or trisubstituted independently of one another by halogen, NH$_2$, —OH or a methoxy residue, R8 is halogen, =O or —(C$_1$-C$_4$)-alkyl, R10 and R20 are the same or different and are independently of one another hydrogen atom, halogen, —(C$_1$-C$_6$)-alkyl, or —(C$_0$-C$_3$)-alkyl-(C$_3$-C$_6$)-cycloalkyl, and R16 is hydrogen atom, in all its stereoisomeric forms and mixtures thereof in any ratio, and its physiologically tolerable salts.

As used herein, the term alkyl is to be understood in the broadest sense to mean hydrocarbon residues which can be linear, i.e. straight-chain or branched. All these statements also apply if an alkyl group occurs as a substituent on another residue, for example in an alkyloxy residue, an alkyloxycarbonyl residue or an arylalkyl residue.

Examples of "—(C$_1$-C$_8$)-alkyl" or "—(C$_1$-C$_8$)-alkylene" are alkyl residues containing 1, 2, 3, 4, 5, 6, 7 or 8 carbon atoms are methyl, methylene, ethyl, ethylene, propyl, propylene, butyl, butylene, pentyl, pentylene, hexyl, heptyl or octyl, the n-isomers of all these residues, isopropyl, isobutyl, 1-methylbutyl, isopentyl, neopentyl, 2-methylpentyl, 2,2-dimethylbutyl, 3-methylpentyl, isohexyl, sec-butyl, tBu, tert-pentyl, sec-butyl, tert-butyl or tert-pentyl. The term "—(C$_0$-C$_8$)-alkyl" or "—(C$_0$-C$_8$)-alkylene" is an alkyl residue containing 1, 2, 3, 4, 5, 6, 7 or 8 carbon atoms. The term "—C$_0$-alkyl" or "—C$_0$-alkylene" is a covalent bond.

Examples of —(C$_3$-C$_8$)-cycloalkyl are cycloalkyl residues containing 3, 4, 5, 6, 7 or 8 ring carbon atoms like cyclopropyl, cyclobutyl, cyclopentyl, cyclohexyl, cycloheptyl or cyclooctyl, which can also be substituted and/or unsaturated.

The term "a monocyclic or bicyclic 6- to 14-membered aryl" or "aryl" are understood as meaning aromatic hydrocarbon radicals containing from 6 to 14 carbon atoms in the ring. Examples of aryl radicals are phenyl, naphthyl, for example 1-naphthyl and 2-naphthyl, biphenylyl, for example 2-biphenylyl, 3-biphenylyl and 4-biphenylyl, anthryl or fluorenyl.

The term "-heterocyclyl" refers to a heterocycle in which one or more of the 4- to 15-ring carbon atoms are replaced by heteroatoms such as nitrogen, oxygen or sulfur. Examples are acridinyl, azaindole (1H-pyrrolopyridinyl), azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl.

The term

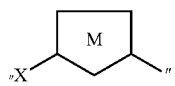

used in formulae I and Ia is a thiophenyl selected from the group

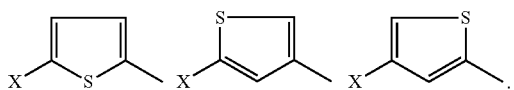

The term "R4 and R5 together with the nitrogen atom to which they are bonded form a 4- to 10-membered mono- or bicyclic heterocyclic ring which in addition to the nitrogen atom can contain one, two or three identical or different ring heteroatoms chosen from oxygen, sulfur and nitrogen" refers to residues, which are selected from compounds such as 2-oxa-5-aza-bicyclo[2.2.1]heptane, azepane, azepine, azetidine, 2,5-diaza-bicyclo[2.2.1]heptane, 1,4-diazepane, 1,2-diazepine, 1,3-diazepine, 1,4-diazepine, 2,3-dihydro-1H-isoindole, 2,3-dihydro-1H-pyrrolo[3,4-c]pyridine, 6,7-dihydro-5H-pyrrolo[3,4-b]pyridine, 5,6-dihydro-4H-pyrrolo[3,4-d]thiazole, dioxazole, dioxazine, imidazole, imidazoline, imidazolidine, isothiazole, isothiazolidine, isothiazoline, isoxazole, isoxazoline, isoxazolidine, 2-isoxazoline, morpholine, octahydro-pyrido[1,2-a]pyrazine, octahydro-pyrrolo[3,4-b]pyridine, octahydro-pyrrolo[1,2-a]pyrazine, [1,4]oxazepane, 1,4-oxazepine, oxazole, piperazine, piperidine, piperidinone, pyrazine, pyrazole, pyrazoline, pyrazolidine, pyridazine, pyridine, pyridone, pyrimidine, pyrrole, pyrrolidine, pyrrolidinone, pyrroline, 4,5,6,7-tetrahydro-1H-imidazo[4,3-c]pyridine, tetrahydropyridine, 1,4,5,6-tetrahydro-pyrrolo[3,4-c]pyrazole, 4,5,6,7-tetrahydro-thiazolo[5,4-c]pyridine, 5,6,7,8-tetrahydro-[1,2,4]triazolo[4,3-a]pyrazine, 4,5,6,7-tetrahydro-thieno[3,2-c]pyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole or 1,2,4-triazole.

The term "R9 and R11 together with the carbon atom to which they are bonded form a 3- to 6 membered carbocyclic ring" refer to structures, which are selected from cyclopropyl, cyclobutyl, cyclopentyl or cyclohexyl.

The term "=O" refers to residues such as carbonyl (—C(O)—), sulfinyl (—S(O)—) or nitroso (—N=O).

The term "—($C_1$-$C_3$)-fluoroalkyl" is a partial or totally fluorinated alkyl-residue, which can be derived from residues such as —$CF_3$, —$CHF_2$, —$CH_2F$, —CHF—$CF_3$, —CHF—$CHF_2$, —CHF—$CH_2F$, —$CH_2$—$CF_3$, —$CH_2$—$CHF_2$, —$CH_2$—$CH_2F$, —$CF_2$—$CF_3$, —$CF_2$—$CHF_2$, —$CF_2$—$CH_2F$, —$CH_2$—CHF—$CF_3$, —$CH_2$—CHF—$CHF_2$, —$CH_2$—CHF—$CH_2F$, —$CH_2$—$CH_2$—$CF_3$, —$CH_2$—$CH_2$—$CHF_2$, —$CH_2$—$CH_2$—$CH_2F$, —$CH_2$—$CF_2$—$CF_3$, —$CH_2$—$CF_2$—$CHF_2$, —$CH_2$—$CF_2$—$CH_2F$, —CHF—CHF—$CF_3$, —CHF—CHF—$CHF_2$, —CHF—CHF—$CH_2F$, —CHF—$CH_2$—$CF_3$, —CHF—$CH_2$—$CHF_2$, —CHF—$CH_2$—$CH_2F$, —CHF—$CF_2$—$CF_3$, —CHF—$CF_2$—$CHF_2$, —CHF—$CF_2$—$CH_2F$, —$CF_2$—CHF—$CF_3$, —$CF_2$—CHF—$CHF_2$, —$CF_2$—CHF—$CH_2F$, —$CF_2$—$CH_2$—$CF_3$, —$CF_2$—$CH_2$—$CHF_2$, —$CF_2$—$CH_2$—$CH_2F$, —$CF_2$—$CF_2$—$CF_3$, —$CF_2$—$CF_2$—$CHF_2$ or —$CF_2$—$CF_2$—$CH_2F$.

The term "=$F_2$" is a fluoro-ethene.

Halogen is fluorine, chlorine, bromine or iodine, preferably fluorine, chlorine or bromine, particularly preferably chlorine or fluorine.

Optically active carbon atoms present in the compounds of the formulae I or Ia can independently of each other have R configuration or S configuration. The compounds of the formula I can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of the formulae I or Ia and it comprises all ratios of the stereoisomers in the mixtures. In case the compounds of the formulae I or Ia can be present as E isomers or Z isomers (or cis isomers or trans isomers) the invention relates both to pure E isomers and pure Z isomers and to E/Z mixtures in all ratios. The invention also comprises all tautomeric forms of the compounds of the formulae I or Ia.

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formulae I or Ia can also be obtained by employing stereochemically uniform starting materials or by using stereoselective reactions.

Physiologically tolerable salts of the compounds of formulae I or Ia are nontoxic salts that are physiologically acceptable, in particular pharmaceutically utilizable salts. Such salts of compounds of the formula I or Ia containing acidic groups, for example a carboxyl group COOH, are for example alkali metal salts or alkaline earth metal salts such as sodium salts, potassium salts, magnesium salts and calcium salts, and also salts with physiologically tolerable quaternary ammonium ions such as tetramethylammonium or tetraethylammonium, and acid addition salts with ammonia and physiologically tolerable organic amines, such as methylamine, dimethylamine, trimethylamine, ethylamine, triethylamine, ethanolamine or tris-(2-hydroxyethyl)amine. Basic groups contained in the compounds of the formulae I or Ia, for example amino groups or guanidino groups, form acid addition salts, for example with inorganic acids such as hydrochloric acid, hydrobromic acid, sulfuric acid, nitric acid or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid or p-toluenesulfonic acid. Compounds of the formulae I or Ia, which simultaneously contain a basic group and an acidic group, for example a guanidino group and a carboxyl group, can also be present as zwitterions (betaines), which are likewise included in the present invention.

Salts of compounds of the formulae I or Ia can be obtained by customary methods known to those skilled in the art, for example by combining a compound of the formulae I or Ia with an inorganic or organic acid or base in a solvent or dispersant, or from other salts by cation exchange or anion exchange. The present invention also includes all salts of the compounds of the formulae I or Ia which, because of low physiologically tolerability, are not directly suitable for use in pharmaceuticals but are suitable, for example, as intermediates for carrying out further chemical modifications of the compounds of the formulae I or Ia or as starting materials for the preparation of physiologically tolerable salts. The present invention furthermore includes all solvates of compounds of the formulae I or Ia for example hydrates or adducts with alcohols. The invention also includes derivatives and modifications of the compounds of the formula I, for example prodrugs, protected forms and other physiologically tolerable derivatives, as well as active metabolites of the compounds of the formulae I or Ia. The invention relates in particular to prodrugs and protected forms of the compounds of the formulae I or Ia, which can be converted into compounds of the formulae I or Ia under physiological conditions. Suitable prodrugs for the compounds of the formulae I or Ia, i.e. chemically modified derivatives of the compounds of the formulae I or Ia having properties which are improved in a desired manner, for example with respect to solubility, bioavailability or duration of action, are known to those skilled in the art. More detailed information relating to prodrugs is found in standard literature like, for example, Design of Prodrugs, H. Bundgaard (ed.), Elsevier, 1985; Fleisher et al., Advanced Drug Delivery Reviews 19 (1996) 115-130; or H. Bundgaard, Drugs of the Future 16 (1991) 443 which are all incorporated herein by reference. Suitable prodrugs for the compounds of the formulae I or Ia are especially acyl prodrugs and carbamate prodrugs of acylatable nitrogen-containing groups such as amino groups and the guanidino group and also ester prodrugs and amide prodrugs of carboxylic acid groups which may be present in compounds of the formulae I or Ia. In the acyl prodrugs and carbamate prodrugs one or more, for example one or two, hydrogen atoms on nitrogen atoms in such groups are replaced with an acyl group or a carbamate, preferably a —($C_1$-$C_6$)-alkyloxycarbonyl group. Suitable acyl groups and carbamate groups for acyl prodrugs and carbamate prodrugs are, for example, the groups $R^{p1}$—CO— and $R^{p2}$O—CO—, in which $R^{p1}$ is hydrogen, ($C_1$-$C_{18}$)-alkyl, ($C_3$-$C_8$)-cycloalkyl, ($C_3$-$C_8$)-cycloalkyl-($C_1$-$C_4$)-alkyl-, ($C_6$-$C_{14}$)-aryl, Heterocyclyl-, ($C_6$-$C_{14}$)-aryl-($C_1$-$C_4$)-alkyl- or Heterocyclyl-($C_1$-$C_4$)-alkyl- and in which $R^{p2}$ has the meanings indicated for $R^{p1}$ with the exception of hydrogen.

The compounds of the formulae I or Ia can be prepared by utilizing procedures and techniques, which per se are well known and appreciated by one of ordinary skill in the art. Starting materials or building blocks for use in the general synthetic procedures that can be applied in the preparation of the compounds of formulae I or Ia are readily available to one of ordinary skill in the art. In many cases they are commercially available or have been described in the literature. Otherwise they can be prepared from readily available precursor compounds analogously to procedures described in the literature, or by procedures or analogously to procedures described in this application. In general, compounds of the formulae I or Ia can be prepared, for example in the course of a convergent synthesis, by linking two or more fragments which can be derived retrosynthetically from the formula I and Ia.

In the preparation of the compounds of the formula I and Ia it can be advantageous or necessary to protect functional groups in the course of the synthesis, which could lead to undesired reactions or side reactions in a synthesis step. Protecting groups (or blocking groups) that may be present on functional groups include allyl, tert.-butyl, benzyl, allyloxycarbonyl(Alloc), tert-butoxycarbonyl(Boc), benzyloxycarbonyl(Z) and 9-fluorenylmethoxycarbonyl(Fmoc) as protecting groups for amino and amidino groups. Ester, alkyl, aryl and sibyl protecting groups may be used to block hydroxyl groups. Carboxylic acids may be protected as esters for example methyl, ethyl and benzyl.

In particular, in the preparation of the compounds of the formula I and Ia building blocks can be connected by performing one or more condensation reactions and/or addition reactions such as amide couplings, e.g. by forming an amide bond between a carboxylic acid group of one building block and an amino group of another building block or sulfonamide couplings, e.g. by forming a sulfonamide bond between a sulfonyl chloride group of one building block and an amino group of another building block. For example, compounds of the formula I and Ia can be prepared retrosynthetically by coupling of building blocks of the formulae II, and III to suitable protected central core IV.

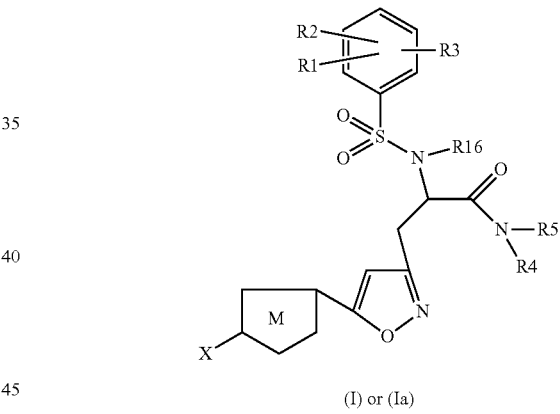

(I) or (Ia)

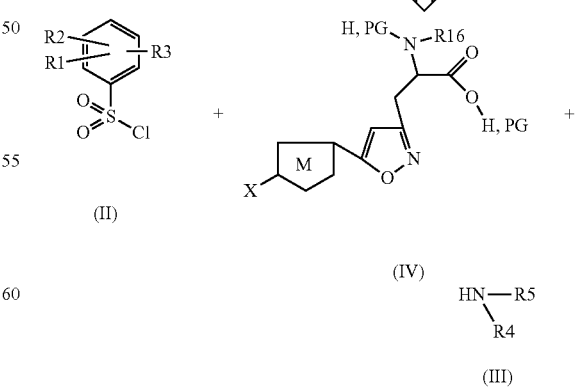

PG = protecting group

These reactions can be carried out in any order depending on the protecting groups employed.

Various general methods for the formation of an amide bond that can be employed in the synthesis of the compounds of formula I and Ia are well known to those skilled in the art, for example from peptide chemistry. An amide coupling step can favorably be carried out by employing a free carboxylic acid activating that carboxylic acid group, preferably in situ, by means of a customary coupling reagent such as a carbodiimide like dicyclohexylcarbodiimide (DCC) or diisopropylcarbodiimide (DIC), or an N,N'-carbonyldiazole like N,N'-carbonyldiimidazole, or a uronium salt like O-((cyano-(ethoxycarbonyl)methylene)amino)-1,1,3,3-tetramethyluronium tetrafluoroborate or O-(7-azabenzotriazol-1-yl)-1,1,3,3-tetramethyluronium hexafluorophosphate, or a chloroformic acid ester like ethyl chloroformate or isobutyl chloroformate, or tosyl chloride, or propylphosphonic acid anhydride, or others, and then reacting the activated carboxylic acid derivative with an amino compound. An amide bond can also be formed by reacting an amino compound with a carboxylic acid halide, in particular a carboxylic acid chloride, which can be prepared in a separate step or in situ from a carboxylic acid and, for example, thionyl chloride, or an carboxylic acid ester or thioester, for example a methyl ester, ethyl ester, phenyl ester, nitrophenyl ester, pentafluorophenyl ester, methylthio ester, phenylthio ester or pyridin-2-ylthio ester.

The activation reactions and coupling reactions are usually performed in the presence of an inert solvent, for example in the presence of an aprotic solvent like dimethylformamide, tetrahydrofuran, dichloromethane, dimethylsulfoxide, hexamethyl phosphoric triamide (HMPT), 1,2-dimethoxyethane (DME), dioxane, or others, or in a mixture of such solvents. Depending on the specific process, the reaction temperature may be varied over a wide range and be, for example, from about −20° C. to the boiling temperature of the solvent or diluent. Also depending on the specific process, it may be necessary or advantageous to add in a suitable amount of one or more auxiliary agents, for example a base like a tertiary amine, such as triethylamine or diisopropylethylamine, or an alkali metal alcoholate, such as sodium methoxide or potassium tert-butoxide, for adjusting the pH or neutralizing an acid that is formed or for liberating the free base of an amino compound that is employed in the form of an acid addition salt, or an N-hydroxyazole like 1-hydroxybenzotriazole, or a catalyst like 4-dimethylaminopyridine. Details on methods for the preparation of activated carboxylic acid derivatives and the formation of amide bonds and ester bonds as well as source literature are given in various standard references like, for example, J. March, Advanced Organic Chemistry, 4th ed., John Wiley & Sons, 1992; or Houben-Weyl, Methoden der organischen Chemie [Methods of Organic Chemistry], Georg Thieme Verlag.

Protecting groups (PG) that may still be present in the products obtained in the coupling reaction are then removed by standard procedures. For example, tert-butyl protecting groups, in particular a tert-butoxycarbonyl group which is used for protection of an amino group, can be deprotected, i.e. converted into the amino group, by treatment with strong acids (e.g. hydrochloric acid, trifluoroacetic acid). Methyl esters which are used for protection of an acid group may be converted into the free acid by treatment with strong bases (e.g. LiOH, NaOH, KOH) or strong acids (e.g. HCl) in the presence of water. As already explained, after the coupling reaction also functional groups can be generated from suitable precursor groups. In addition, a conversion into a physiologically tolerable salt can then be carried out by known processes.

In general, a reaction mixture containing a final compound of the formula I or Ia or an intermediate is worked up and, if desired, the product is then purified by customary processes known to those skilled in the art. For example, a synthesized compound can be purified using well known methods such as crystallization, chromatography or reverse phase-high performance liquid chromatography (RP-HPLC) or other methods of separation based, for example, on the size, charge or hydrophobicity of the compound. Similarly, well known methods such as amino acid sequence analysis, NMR, IR and mass spectrometry (MS) can be used for characterizing a compound of the invention.

The compounds of the formula I and Ia, which on account of their chemical structure occur in enantiomeric or diastereomeric forms, can be prepared in enantiomeric pure form employing enantiomerically pure starting material or can be resolved into the pure enantiomers by salt formation with enantiomerically pure acids or bases, chromatography on chiral stationary phases or derivatization by means of chiral enantiomerically pure compounds such as amino acids, separation of the diastereomers thus obtained, and removal of the chiral auxiliary groups.

The compounds of the formula I and Ia can be isolated either in free form or, in the case of the presence of acidic or basic groups, converted into physiologically tolerable salts. The preparation of physiologically tolerable salts of compounds of the formula I and Ia capable of salt formation, including their stereoisomeric forms, is carried out in a manner known per se. With basic reagents such as hydroxides, carbonates, hydrogen carbonates, alkoxides and also ammonia or organic bases, for example trimethyl- or triethylamine, ethanolamine or triethanolamine or alternatively basic amino acids, for example lysine, ornithine or arginine, the carboxylic acids form stable alkali metal, alkaline earth metal or optionally substituted ammonium salts. If the compounds of the formula I and Ia contain basic groups, stable acid addition salts can be prepared using strong acids e.g. both inorganic and organic acids such as hydrochloric, hydrobromic, sulfuric, phosphoric, methanesulfonic, benzenesulfonic, p-toluenesulfonic, 4-bromobenzenesulfonic, cyclohexylamidosulfonic, trifluoromethyl-sulfonic, acetic, oxalic, tartaric, succinic or trifluoroacetic acid are suitable.

Compounds I and Ia of this application may especially be prepared by coupling of a sulfonyl chloride of formula II to isoxazole-amino acid methyl esters of formula V leading to intermediates of formula VI (scheme 1). After ester saponification leading to intermediates of formula VII the final structures I or Ia may be prepared by amide coupling to a compound of formula III:

Scheme 1:

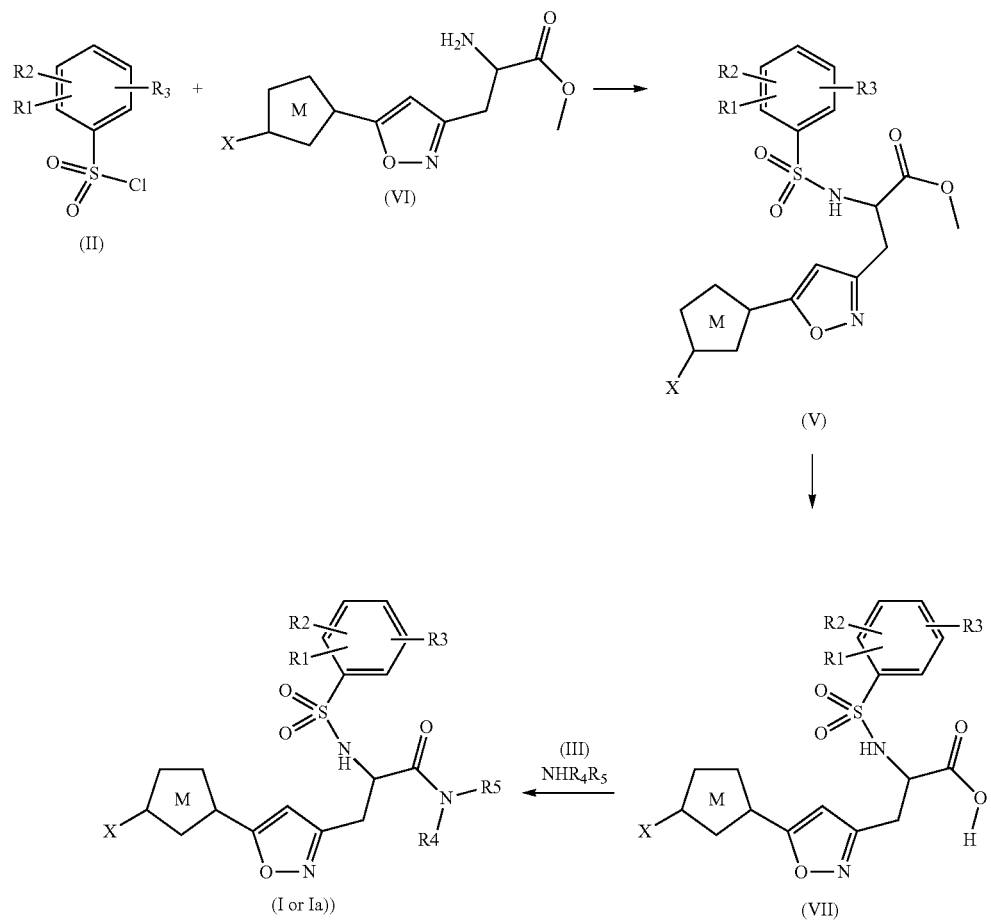

The starting compounds of the formulae II, III and VI and other compounds which are employed in the synthesis of the compounds of formula I and Ia for introducing certain structural units, are commercially available or can be readily prepared from commercially available compounds or by analogous procedures described below or in the literature which is readily available to those skilled in the art.

A compound of formula V may be converted to a compound VII by standard ester saponification methodology, e.g. (LiOH/THF/water) as described earlier.

Compounds of formula VII can be converted to final compounds I and Ia by standard amide coupling technology to a compound of formula III (scheme 1).

Compounds of formula II are either commercially available or prepared according to the procedures given in the schemes and examples below.

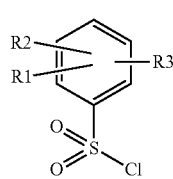

In general, functionalized sulfonyl chlorides of formula II can be prepared by many routes described in the literature. For example aryl lithium derivatives can be treated with $SO_2$ and the resulting sulfinates can be chlorinated with N-chlorosuccinimide. Another example for a suitable precursor for the sulfonyl chloride of formula II can be the corresponding sulfides VIII which are commercially available or prepared according to the procedures given in the schemes and examples below. Such sulfides VIII can be transformed to the corresponding sulfonyl chlorides of formula II by means of an oxidative chlorination procedure employing for example chlorine, N-chlorosuccinimide or $SO_2Cl_2$/acetic acid as illustrated in scheme 2:

Scheme 2:

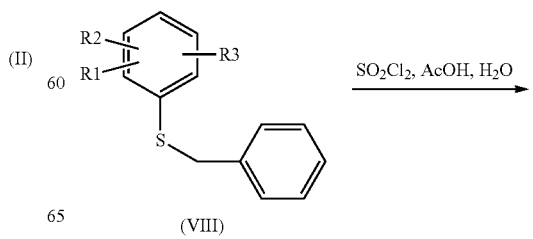

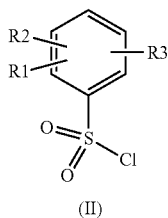

(II)

Sulfides of formula VIII may generally be prepared by transition metal catalyzed transformation of aryl halides with the corresponding thiols or by nucleophilic aromatic substitution of aryl fluorides or by metal-lithium exchange of aryl halides and subsequent trapping of the lithiated species with sulfur and a suitable benzylation reagent like benzylbromide (scheme 3):

Scheme 3:

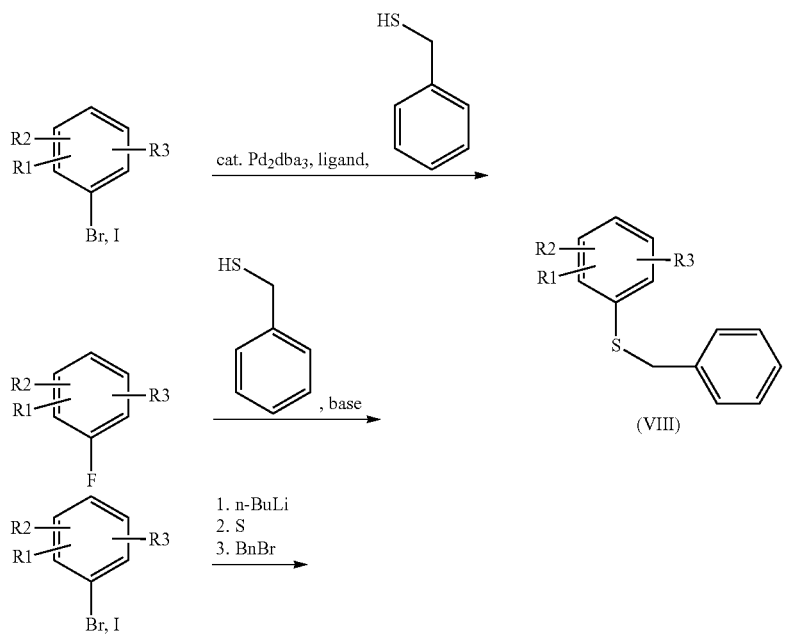

In the following, procedures of particular interest for the embodiment of this invention are listed and referenced briefly, however, they are standard procedures discussed in the literature, and are well known to one skilled in the art. Although not always shown explicitly, in certain cases isomers will occur during the synthesis of the below mentioned reactions. Nevertheless such mixtures of isomers can be separated by modern separation techniques like, for example, preparative HPLC.

1) Functionalization of Aryl Rings by Deprotonation and Subsequent Trapping with Electrophiles:

For example, activated aryl rings systems like 1,3-dibromobenzene may be deprotonated using strong bases like LDA and subsequently trapped with electrophiles like alkyl halides or formylating agents like DMF (scheme 4):

Scheme 4:

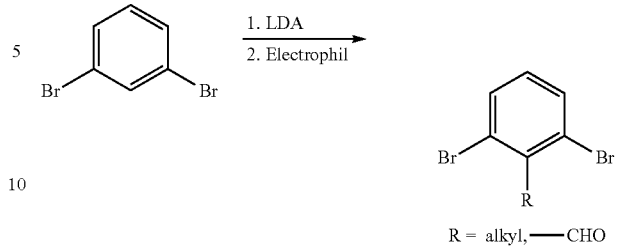

R = alkyl, —CHO

2) Functionalization of Aryl Rings by Transition Metal Catalyzed Reactions:

Modern cross coupling technology as widely described in numerous reviews (see references below) allows for selective functionalization of aryl ring systems by means of cross couplings employing suitable coupling partners.

For example a Suzuki-coupling may be carried out using and aryl halide or triflate and a boronic-acid coupling partner (scheme 5). Alternatively, these types of couplings may for example also be performed by using an aryl halide and an organo tin or an organo zinc coupling partner by means of a Stille or Negishi-coupling respectively (scheme 5):

Scheme 5:

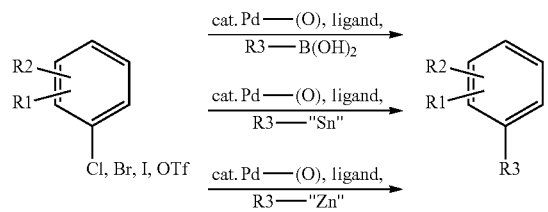

It is well understood by one skilled in the art that these couplings may be carried out in an inverted fashion of coupling partners, for example by exchanging the functionalities of the corresponding coupling partners (scheme 6):

Scheme 6:

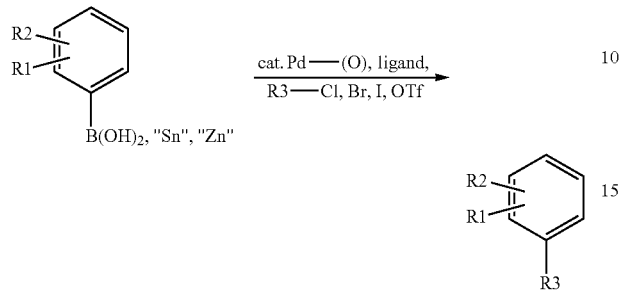

In another example aryl halides may be converted to amines or amides by transition metal catalyzed reactions. Scheme 7 illustrates the case of aryl halides being converted to amines or amides employing copper or palladium-catalyzed reactions.

Scheme 7:

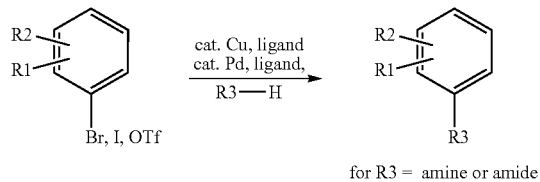

References for transition-metal catalyzed chemistry: (F. Diederich, P. Stang, Metal-catalyzed Cross-coupling Reactions, Wiley-VCH, 1998; or M. Beller, C. Bolm, Transition Metals for Organic Synthesis, Wiley-VCH, 1998; J.

3) Synthesis of Ethers:

For example phenolic —OH groups may be converted to ethers by treatment with suitable electrophiles in the presence of a base. O-alkyl ether may be prepared by using an alkyl halide in the presence of a base. Alternatively, ethers may be prepared from phenols and alcohols using PPh₃/DIAD by means of a Mitsunobu reaction. Scheme 8 shows representative procedures:

Scheme 8:

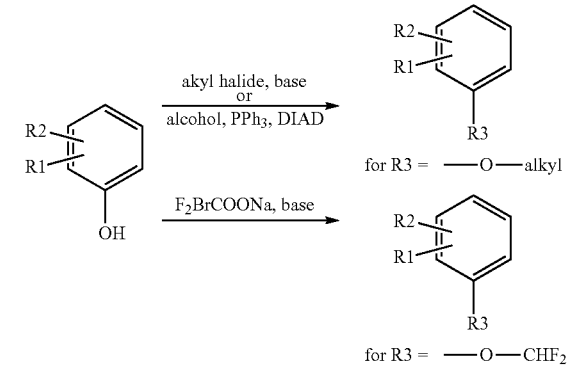

4) Ester-Saponification:

Ester groups present can be hydrolyzed to the corresponding carboxylic acids, which after activation can then be reacted with amines or alcohols under standard conditions to give amides or esters, respectively.

Amino acid esters of general formula V may be prepared by many different routes described in the literature. Reactions may also be carried out under control of the configuration of the stereocenter. Strategies to achieve such enantiomeric enriched or enantiomeric pure compounds are widely described in the original literature. For a review see: R. O. Duthaler, Tetrahedron, 1994, 1539-1650. Compounds of formula V may especially be prepared by a strategy originally described by and known as the Schöllkopf-method (U. Schöllkopf et al., Synthesis, 861-864). In this respect a isoxazole bromide of general formula IX may be reacted with commercially available (R)-2-isopropyl-3,6-dimethoxy-2,5-dihydro-pyrazine X to yield a diastereomeric enriched mixture in favor of component XIa (scheme 9). After separation of the main component XIa from XIb the chiral auxiliary may be hydrolyzed to form the amino acid ester V in enantiomerically pure form Va.

Scheme 9:

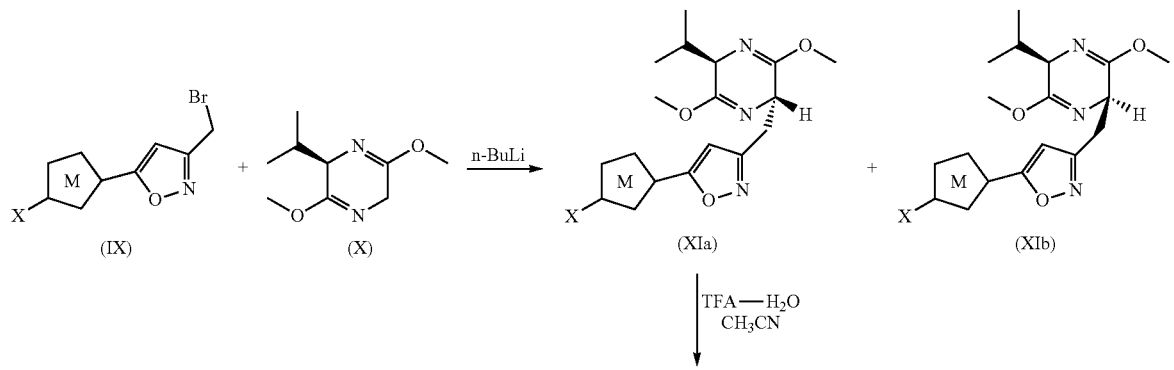

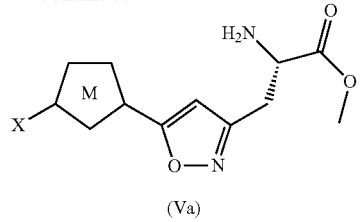

(Va)

General:

The previously-mentioned reactions for the conversion of functional groups are furthermore, in general, extensively described in textbooks of organic chemistry like M. Smith, J. March, March's Advanced Organic Chemistry, Wiley-VCH, 2001 and in A. Katritzky, C. Rees, E. Scriven Comprehensive Heterocyclic Chemistry II, Elsevier Science, 1996, in which details on the reactions and primary source literature can be found. In the present case it may in certain cases become necessary to specifically adapt reaction conditions or to choose specific reagents from a variety of reagents that can in principle be employed in a conversion reaction, or otherwise to take specific measures for achieving a desired conversion, for example to use protecting group techniques. However, finding out suitable reaction variants and reaction conditions in such cases does not cause any problems for one skilled in the art.

Amide-Couplings:

N-Acylation of a nitrogen atom, for example with substituted thiophene carboxylic acid derivatives to produce finally compounds of the formulae I or Ia, can, for example, be performed under standard conditions by means of common coupling reagents used in peptide synthesis. Such coupling reagents are, for example, carbodiimides like dicyclohexyl-carbodiimide (DCC) or diisopropylcarbodiimide, carbonyl-diazoles like carbonyldiimidazole (CD) and similar reagents, propylphosphonic anhydride, O-((cyano-(ethoxycarbonyl)-methylene)amino)-N,N,N',N'-tetramethyluronium tetrafluo-roborate, O-(7-aza-benzotriazole-1-yl)-N,N,N',N'-tetram-ethyluronium-hexafluorophosphate, diethylphosphoryl cyanide (DEPC) or bis-(2-oxo-3-oxazolidinyl)-phosphoryl chloride (BOP-Cl) and many others. N-Acylation can also be performed by the reaction with a corresponding acid-chloride, -fluoride or -bromide or a corresponding anhydride.

The compounds of the present invention are serine protease inhibitors, which inhibit the activity of the blood coagulation enzymes factor Xa and thrombin. They are specific serine protease inhibitors inasmuch as they do not substantially inhibit the activity of other proteases whose inhibition is not desired. The activity of the compounds of the formulae I or Ia can be determined, for example, in the assays described below or in other assays known to those skilled in the art. With respect to factor Xa and thrombin inhibition, a preferred embodiment of the invention comprises compounds which have a Ki<1 mM for factor Xa inhibition and thrombin inhibition as determined in the assays described below and which preferably do not substantially inhibit the activity of other proteases involved in coagulation and fibrinolysis whose inhibition is not desired (using the same concentration of the inhibitor). The compounds of the invention inhibit factor Xa catalytic activity either directly, within the prothrombinase complex or as a soluble subunit, or indirectly, by inhibiting the assembly of factor Xa into the prothrombinase complex.

As inhibitors of factor Xa and thrombin the compounds of the formulae I or Ia and their physiologically tolerable salts are generally suitable for the therapy and prophylaxis of conditions in which the activity of factor Xa and/or thrombin plays a role or has an undesired extent, or which can favorably be influenced by inhibiting factor Xa and thrombin or decreasing their activities, or for the prevention, alleviation or cure of which an inhibition of factor Xa and thrombin or a decrease in their activity is desired by the physician. As inhibition of factor Xa and thrombin influences blood coagulation and fibrinolysis, the compounds of the formulae I or Ia and their physiologically tolerable salts are generally suitable for reducing blood clotting, or for the therapy and prophylaxis of conditions in which the activity of the blood coagulation system plays a role or has an undesired extent, or which can favorably be influenced by reducing blood clotting, or for the prevention, alleviation or cure of which a decreased activity of the blood coagulation system is desired by the physician. A specific subject of the present invention thus are the reduction or inhibition of unwanted blood clotting, in particular in an individual, by administering an effective amount of a compound of the formula I or a physiologically tolerable salt, as well as pharmaceutical preparations therefor.

The present invention also relates to the use of the compounds of the formulae I or Ia and/or their physiologically tolerable salts for the production of pharmaceuticals for inhibition of factor Xa and thrombin or for influencing blood coagulation, inflammatory response or fibrinolysis or for the therapy or prophylaxis of the diseases mentioned above or below, for example for the production of pharmaceuticals for the therapy and prophylaxis of cardiovascular disorders, thromboembolic diseases or restenoses. The invention also relates to the use of the compounds of the formulae I or Ia and/or their physiologically tolerable salts for the inhibition of factor Xa and thrombin or for influencing blood coagulation or fibrinolysis or for the therapy or prophylaxis of the diseases mentioned above or below, for example for use in the therapy and prophylaxis of cardiovascular disorders, thromboembolic diseases or restenoses, and to methods of treatment aiming at such purposes including methods for said therapies and prophylaxis.

The present invention also relates to pharmaceutical preparations (or pharmaceutical compositions) which contain an effective amount of at least one compound of the formulae I or Ia and/or its physiologically tolerable salts in addition to a customary pharmaceutically acceptable carrier, i.e. one or more pharmaceutically acceptable carrier substances or excipients and/or auxiliary substances or additives.

The invention also relates to the treatment of disease states such as abnormal thrombus formation, acute myocardial infarction, unstable angina, thromboembolism, acute vessel closure associated with thrombolytic therapy or percutaneous transluminal coronary angioplasty (PTCA), transient ischemic attacks, stroke, intermittent claudication or bypass grafting of the coronary or peripheral arteries, vessel luminal narrowing, restenosis post coronary or venous angioplasty, maintenance of vascular access patency in long-term hemodialysis patients, pathologic thrombus formation occurring in the veins of the lower extremities following abdominal, knee or hip surgery, pathologic thrombus formation occurring in the veins of the lower extremities following abdominal, knee and hip surgery, a risk of pulmonary thromboembolism, or disseminated systemic intravascular coagulatopathy occurring in vascular systems during septic shock, certain viral infections or cancer.

The compounds of the present invention can also be used to reduce an inflammatory response. Examples of specific disorders for the treatment or prophylaxis of which the compounds of the formulae I or Ia can be used are coronary heart disease, myocardial infarction, angina pectoris, vascular restenosis, for example restenosis following angioplasty like PTCA, adult respiratory distress syndrome, multi-organ failure and disseminated intravascular clotting disorder. Examples of related complications associated with surgery are thromboses like deep vein and proximal vein thrombosis, which can occur following surgery.

The compounds of the formulae I or Ia and their physiologically tolerable salts can be administered to animals, preferably to mammals, and in particular to humans as pharmaceuticals for therapy or prophylaxis. They can be administered on their own, or in mixtures with one another or in the form of pharmaceutical preparations, which permit enteral or parenteral administration.

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carriers being used in addition to the compound(s) of the formulae I or Ia and/or its (their) physiologically tolerable salts. For the production of pills, tablets, coated tablets and hard gelatin capsules it is possible to use, for example, lactose, cornstarch or derivatives thereof, talc, stearic acid or its salts, etc. Carriers for soft gelatin capsules and suppositories are, for example, fats, waxes, semisolid and liquid polyols, natural or hardened oils. Suitable carriers for the production of solutions, for example injection solutions, or of emulsions or syrups are, for example, water, saline, alcohols, glycerol, polyols, sucrose, invert sugar, glucose, vegetable oils, etc. Suitable carriers for microcapsules, implants or rods are, for example, copolymers of glycolic acid and lactic acid. The pharmaceutical preparations normally contain about 0.5% to 90% by weight of the compounds of the formulae I or Ia and/or their physiologically tolerable salts. The amount of the active ingredient of the formulae I or Ia and/or its physiologically tolerable salts in the pharmaceutical preparations normally is from about 0.5 mg to about 1000 mg, preferably from about 1 mg to about 500 mg.

In addition to the active ingredients of the formulae I or Ia and/or their physiologically acceptable salts and to carrier substances, the pharmaceutical preparations can contain additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formulae I or Ia, and/or their physiologically tolerable salts. In case a pharmaceutical preparation contains two or more compounds of the formulae I or Ia, the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formulae I or Ia allows a great deal of control over the biological and physico-chemical properties of the compounds and thus allows the selection of such desired compounds. Furthermore, in addition to at least one compound of the formulae I or Ia and/or a physiologically tolerable salt, the pharmaceutical preparations can also contain one or more other therapeutically or prophylactically active ingredients.

When using the compounds of the formulae I or Ia the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from 0.01 mg/kg to 100 mg/kg, preferably from 0.1 mg/kg to 50 mg/kg, in particular from 0.1 mg/kg to 10 mg/kg, (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

A compound of the formulae I or Ia can also advantageously be used as an anticoagulant outside an individual. For example, an effective amount of a compound of the invention can be contacted with a freshly drawn blood sample to prevent coagulation of the blood sample. Further, a compound of the formulae I or Ia or its salts can be used for diagnostic purposes, for example in in vitro diagnoses, and as an auxiliary in biochemical investigations. For example, a compound of the formulae I or Ia can be used in an assay to identify the presence of factor Xa or thrombin or to isolate factor Xa or thrombin in a substantially purified form. A compound of the invention can be labeled with, for example, a radioisotope, and the labeled compound bound to factor Xa or thrombin is then detected using a routine method useful for detecting the particular label. Thus, a compound of the formulae I or Ia or a salt thereof can be used as a probe to detect the location or amount of factor Xa and thrombin activity in vivo, in vitro or ex vivo.

The general synthetic sequences for preparing the compounds useful in the present invention are outlined in the examples given below. Both an explanation of, and the actual procedure for, the various aspects of the present invention are described where appropriate. The following examples are intended to be merely illustrative of the present invention, and not limiting thereof in either scope or spirit. Those with skill in the art will readily understand that known variations of the conditions and processes described in the examples can be used to synthesize the compounds of the present invention.

When in the final step of the synthesis of a compound an acid such as trifluoroacetic acid or hydrochloric acid was used, for example when trifluoroacetic acid was employed to remove a tBu group or when a compound was purified by chromatography using an eluent which contained such an acid, in some cases, depending on the work-up procedure, for example the details of a freeze-drying process, the compound was obtained partially or completely in the form of a salt of the acid used, for example in the form of the trifluoroacetic acid salt or hydrochloric acid salt.

It is understood that modifications that do not substantially affect the activity of the various embodiments of this invention are included within the invention disclosed herein. Accordingly, the following examples are intended to illustrate but not limit the present invention.

ABBREVIATIONS USED acetic acid AcOH
acetonitrile AcN
aqueous aq
n-Butyllithium n-BuLi
tert-Butyl tBu
dibenzylidenacetone dba
Dichloromethane DCM
diastereomeric excess d.e.
Diisopropylethylamine DIPEA
4-Dimethyaminopyridine DMAP
N,N-Dimethylformamide DMF
Dimethylsulfoxide DMSO
O-(7-Azabenzotriazol-1-yl)-N,N,N',N'-tetramethyluronium-hexafluorophosphate HATU
Lithium diisopropylamide LDA
Methanol MeOH
Tert.-butyl methyl ether MTBE
N-Chlorosuccinimide NCS
Room temperature 20° C. to 25° C. RT
Saturated sat.
Tetrahydrofuran THF
Trifluoroacetic acid TFA
O-((Ethoxycarbonyl)cyanomethyleneamino)-N,N,N',N'-tetramethyluronium tetrafluoroborate TOTU
9,9-dimethyl-4,5-bis(diphenylphosphino)xanthene Xantphos Example 1

N-{(S)-2-Azepan-1-yl-1-[5-(5-chloro-thiophen-2-yl)-isoxazol-3-ylmethyl]-2-oxo-ethyl}-2-ethyl-3-(3-oxo-morpholin-4-yl)-benzenesulfonamide 1.1) (2S,5R)-2-[5-(5-Chloro-thiophen-2-yl)-isoxazol-3-ylmethyl]-5-isopropyl-3,6-dimethoxy-2,5-dihydro-pyrazine (Intermediate 1)

Commercially available (R)-2-isopropyl-3,6-dimethoxy-2,5-dihydro-pyrazine (2.0 g, 10.86 mmol) in dry THF (12 ml) under argon was cooled to −75° C. n-BuLi (8 ml, 13.03 mmol, 1.6M solution in hexanes) was added slowly and stirring was continued for 30 min. After that 3-bromomethyl-5-(5-chloro-thiophen-2-yl)-isoxazole (3.628 g, 13.03 mmol), (preparation described in J. Med. Chem. 2005, 4511-4525; Bioorg. Med. Chem. Lett. 2004, 4191-4195), in THF (15 ml) was added dropwise under stirring and stirring was continued for 30 min at −75° C. Then the mixture was warmed to 0° C. and stirred for 1 h before it was quenched with sat. aq. NaHCO$_3$-solution. The mixture was extracted with ethyl acetate, the organic layers were combined and dried with MgSO$_4$, filtered and evaporated to dryness. A crude oil was obtained (4.1 g) and the diastereomeric excess (d.e.: 88%) was determined by H-NMR from that crude mixture. The mixture was separated by column chromatography on silica gel (n-heptane-ethyl acetate 6:1). Yield: 3.3 g, 80%.

1.2) (S)-2-Amino-3-[5-(5-chloro-thiophen-2-yl)-isoxazol-3-yl]-propionic acid methyl ester (Intermediate 2)

Intermediate 1 (3.25 g, 8.51 mmol) in acetonitrile (183 ml) was treated with TFA (90 ml, 2 M in water) and stirred at RT overnight. After complete conversion the mixture was neutralized with sat. aq. NaHCO$_3$-solution, the majority of the acetonitrile was evaporated and the remainder extracted with ethyl acetate. The combined organic phases were washed with brine, dried with MgSO$_4$, filtered and evaporated to dryness. The resulting crude oil (2.5 g) was used in the next steps without further purification.

1.3) 1,3-Dibromo-2-ethyl-benzene (Intermediate 3)

A three necked round-bottom flask was purged with argon and then filled with dry THF (1.2 l), 1,3-dibromo benzene (121 g, 0.514 mol) and ethyl iodide (95.4 g, 0.611 mol). The mixture was cooled to −78° C. and LDA (64.2 g, 0.697 mol) (2 M in THF/n-heptane/ethyl benzene) was added slowly in a way that the temperature did not rise above −65° C. After stirring for 2.75 h the reaction was poured onto 1 l sat. aq. NH$_4$Cl solution and stirred vigorously for 20 min. Two times extraction with DCM yielded colorless oil (167 g) which was used in the next step without further purification.

1.4) 1-Benzylsulfanyl-3-bromo-2-ethyl-benzene (Intermediate 4)

According to J. Org. Chem. 2004, 69, 3236-3239:
Intermediate 3 (528 mg, 2 mmol) in 13 ml THF were cooled to −78° C. and then treated with n-BuLi (1.25 ml, 2 mmol) (1.6 M in heptane). After stirring for 15 min at −78° C. sulfur (64 mg, 2 mmol) was added under argon atmosphere and the reaction temperature was kept at −78° C. for another 30 min. Then benzyl bromide (0.238 ml, 2 mmol) in 2 ml THF was added and stirring at −78° C. was continued for 90 min. The reaction was quenched by addition of 10 ml sat. aq. NH$_4$Cl-solution and 150 ml of H$_2$O. After three times extraction with DCM, the combined organic layers were washed with water, dried with MgSO$_4$, evaporated to dryness and the product was purified by chromatography on silica gel. Yield: 488 mg, 79%

1.5) 4-(3-Benzylsulfanyl-2-ethyl-phenyl)-morpholin-3-one (Intermediate 5)

Intermediate 4 (1.075 g, 3.5 mmol), morpholin-3-one (389 mg, 3.85 mmol), CuI (67 mg, 0.35 mmol), N,N'-dimethylethylene diamine (75 µl, 0.7 mmol) and K$_2$CO$_3$ (1.064 g, 7.7 mmol) were suspended in toluene (30 ml) under argon and heated to 110° C. for 20 h. After cooling to RT the reaction mixture was quenched by addition of 100 ml sat. aq. NH$_4$Cl, 150 ml concentrated NH$_3$ in water and 100 ml water and extracted three times with ethyl acetate. The organic layers were combined and washed with water and sat. aq. NaCl-solution, dried with MgSO$_4$, filtered and evaporated to dryness. The resulting oil crystallizes upon standing and was triturated with n-heptane-MTBE (19:1).
Yield: 974 mg, 85%

1.6) 2-Ethyl-3-(3-oxo-morpholin-4-yl)-benzene-sulfonyl chloride (Intermediate 6)

Intermediate 6 (197 mg, 0.6 mmol) 1.6) was dissolved in 4 ml DCM and treated with water (44 µl, 2.4 mmol), AcOH (138 µl, 2.4 mmol) and $SO_2Cl_2$ (193 µl, 2.4 mmol) at 0° C. After stirring for 5 min at 0° C. and 90 min at RT the reaction was cooled back to 0° C. and quenched by addition of 10 ml water. The aqueous solution was extracted with DCM (three times) and combined organic layers were washed with cold water. Drying over $MgSO_4$ and evaporation to dryness yielded 209 mg of crude intermediate 6 which was used without further purification in the next step.

1.7) (S)-3-[5-(5-Chloro-thiophen-2-yl)-isoxazol-3-yl]-2-[2-ethyl-3-(3-oxo-morpholin-4-yl)-benzene-sulfonylamino]-propionic acid methyl ester (Intermediate 7)

Intermediate 2 (860 mg, 3 mmol) was dissolved in 15 ml DCM and DIPEA (2.041 ml, 12 mmol). 2-ethyl-3-(3-oxo-morpholin-4-yl)-benzenesulfonyl chloride, Intermediate 6 (911 mg, 3 mmol) in 10 ml DCM was slowly added and the reaction was stirred at RT overnight. After that 300 µl DIPEA were added and the reaction mixture was heated to 40° C. for 30 min. Then the solution was evaporated to dryness, dissolved in ethyl acetate, washed with 1 N HCl, sat. aq. $NaHCO_3$ and brine. The combined organic layers were dried with $MgSO_4$, filtered and evaporated to dryness. The crude product (1.5 g) was used without further purification in the next step.

1.8) (S)-3-[5-(5-Chloro-thiophen-2-yl)-isoxazol-3-yl]-2-[2-ethyl-3-(3-oxo-morpholin-4-yl)-benzene-sulfonylamino]-propionic acid (Intermediate 8)

Intermediate 7 (1.5 g, 2.71 mmol) in THF (15 ml), MeOH (5 ml) and water (5 ml) was treated with LiOH (194 mg, 8.12 mmol) and stirred at RT overnight. The mixture was acidified with HCl and extracted with ethyl acetate. The combined organic layers were washed with water and brine, dried with $MgSO_4$, filtered and evaporated to dryness. The crude product (1.3 g) was used without further purification in the next step.

1.9) N-{(S)-2-Azepan-1-yl-1-[5-(5-chloro-thiophen-2-yl)-isoxazol-3-ylmethyl]-2-oxo-ethyl}-2-ethyl-3-(3-oxo-morpholin-4-yl)-benzenesulfonamide To intermediate 8 (300 mg, 0.56 mmol) in DCM/DMF 2:1 (6 ml) was added azepane (55 mg, 0.56 mmol), HATU (253 mg, 0.67 mmol) and DIPEA (189 µl, 1.11 mmol). After stirring overnight the mixture was purified by preparative HPLC. Yield after lyophilization: 84 mg, 24%, colorless, amorphous solid.

MS ($ES^+$): m/e=621.1/623.1, chloro pattern.

Example 2

N-{(S)-2-Azepan-1-yl-1-[5-(5-chloro-thiophen-2-yl)-isoxazol-3-ylmethyl]-2-oxo-ethyl}-2-chloro-3-(3-oxo-morpholin-4-yl)-benzenesulfonamide

2.1) 1-Benzylsulfanyl-3-bromo-2-chloro-benzene (Intermediate 9)

To stirred phenyl-methanethiol (14.8 g, 119.36 mmol) in 175 ml DMF was added $Cs_2CO_3$ (38.89 g, 119.36 mmol) under argon. After 10 min. 1-bromo-2-chloro-3-fluoro-benzene (25 g, 119.36 mmol) in 25 ml DMF was added and stirring was continued overnight at RT and then 3 h at 80° C. After cooling the mixture was diluted with ethyl acetate/water and washed subsequently with 1 N HCl and brine. The organic layer was dried with $MgSO_4$, filtered and evaporated. Purification by chromatography on silica gel yielded 22 g (59%) as an amorphous, colorless solid.

2.2) 4-(3-Benzylsulfanyl-2-chloro-phenyl)-morpholin-3-one (Intermediate 10)

Intermediate 9 (10 g, 31.38 mmol) was treated with morpholin-3-one (389 mg, 3.85 mmol) according to the procedure described in example 1; 1.5).

Yield after chromatography on silica gel (n-heptane-ethyl acetate): 7.2 g (68%).

2.3) 2-Chloro-3-(3-oxo-morpholin-4-yl)-benzene-sulfonyl chloride (Intermediate 11)

Intermediate 10 (1 g, 3.05 mmol) was converted to the title sulfonyl chloride using the procedure described in example 1; 1.6). The crude material was used without further purification in the next step.

2.4) (S)-2-[2-Chloro-3-(3-oxo-morpholin-4-yl)-benzenesulfonylamino]-3-[5-(5-chloro-thiophen-2-yl)-isoxazol-3-yl]-propionic acid methyl ester (Intermediate 12)

Intermediate 2 (516 mg, 1.80 mmol) and intermediate 11 (558 mg, 1.8 mmol) were coupled using the procedure described in example 1; 1.7. After workup the crude product was used without further purification in the next step.

2.5) (S)-2-[2-Chloro-3-(3-oxo-morpholin-4-yl)-benzenesulfonylamino]-3-[5-(5-chloro-thiophen-2-yl)-isoxazol-3-yl]-propionic acid (Intermediate 12)

Intermediate 11 (840 mg, 1.50 mmol) was saponified using the procedure described in example 1; 1.8. After workup the crude product was used without further purification in the next step.

2.6) N-{(S)-2-Azepan-1-yl-1-[5-(5-chloro-thiophen-2-yl)-isoxazol-3-ylmethyl]-2-oxo-ethyl}-2-chloro-3-(3-oxo-morpholin-4-yl)benzenesulfonamide Intermediate 12 (300 mg, 0.55 mmol) and azepane (54 mg, 0.55 mmol) were coupled using the procedure described in example 1; 1.9.

The mixture was purified by preparative HPLC. Yield after lyophilization: 127 mg, 37%, colorless, amorphous solid. MS ($ES^+$): m/e=627.0/629.0, chloro pattern.

Example 3

(S)-3-[5-(5-Chloro-thiophen-2-yl)-isoxazol-3-yl]-N-cyclopropylmethyl-2-[5-fluoro-2-methoxy-3-(2-oxo-piperidin-1-yl)-benzenesulfonylamino]-propiona-mide

3.1) 1-Benzylsulfanyl-3-bromo-5-fluoro-2-methoxy-benzene (Intermediate 13)

1,3-Dibromo-5-fluoro-2-methoxy-benzene (14.2 g, 50 mmol), phenyl-methanethiol (5.86 ml, 50 mmol), $Pd_2$ $dba_3$ (1.145 g, 1.25 mmol, 2.5 mol-%), Xantphos (1.447 g, 2.5 mmol, 5 mol-%) and DIPEA (17.5 ml, 100 mmol) were dissolved in 130 ml dry, degassed 1,4-dioxane and heated to reflux for 3 hours. After cooling down the mixture was filtrated and evaporated. The remaining solid (22 g) was chromatographed on silica gel using n-heptane-MTBE as eluent. Yield: 12.42 g, 76%

3.2) 1-(3-Benzylsulfanyl-5-fluoro-2-methoxy-phenyl)piperidin-2-one (Intermediate 14)

Intermediate 13 (4.22 g, 12.9 mmol) was treated with piperidin-2-one (1.41 g, 14.2 mmol) according to the procedure described in 1.5). Yield after triturating (with n-heptane-ethyl acetate, 4:1) and filtration: 2.67 g (60%), crystalline solid.

3.3) 5-Fluoro-2-methoxy-3-(2-oxo-piperidin-1-yl) benzenesulfonyl chloride (Intermediate 15)

Intermediate 14 (1.6 g, 4.63 mmol) was converted to the title compound sulfonyl chloride using the procedure described in example 1; 1.6). The crude material was used without further purification in the next step.

3.4) (S)-3-[5-(5-Chloro-thiophen-2-yl)-isoxazol-3-yl]-2-[5-fluoro-2-methoxy-3-(2-oxo-piperidin-1-yl)-benzenesulfonylamino]-propionic acid methyl ester (Intermediate 16)

Intermediate 2 (1.604 g, 5.59 mmol) and intermediate 15 (1.80 g, 5.59 mmol) were coupled using the procedure described in example 1; 1.7). After workup the crude product was used without further purification in the next step.

3.5) (S)-3-[5-(5-Chloro-thiophen-2-yl)-isoxazol-3-yl]-2-[5-fluoro-2-methoxy-3-(2-oxo-piperidin-1-yl)-benzenesulfonylamino]-propionic acid (Intermediate 17)

Intermediate 16 (2.8 g, 4.89 mmol) was saponified using the procedure described in example 1; 1.8). After workup the crude product was used without further purification in the next step.

3.6) (S)-3-[5-(5-Chloro-thiophen-2-yl)-isoxazol-3-yl]-N-cyclopropylmethyl-2-[5-fluoro-2-methoxy-3-(2-oxo-piperidin-1-yl)-benzenesulfonylamino]-propionamide Intermediate 17 (350 mg, 0.63 mmol) and cyclopropylmethylamine (45 mg, 0.63 mmol) were coupled using the procedure described in example 1; 1.9), where only 25% conversion of starting materials was discovered. Heating to 50° C. did not lead to further conversion. Then TOTU (246 mg, 0.75 mmol) was added and after stirring for 1 h at RT conversion was completed. The mixture was purified by preparative HPLC. Yield after lyophilization: 162 mg, 43%, colorless, amorphous solid.

MS (ES$^+$): m/e=611.1/613.1, chloro pattern.

Example 4

N—[(S)-1-[5-(5-Chloro-thiophen-2-yl)-isoxazol-3-ylmethyl]-2-(4-cyclopropyl-piperazin-1-yl)-2-oxo-ethyl]-5-fluoro-2-methoxy-3-(2-oxo-piperidin-1-yl)-benzenesulfonamide trifluoro acetate Intermediate 17 (150 mg, 0.27 mmol; see example 3) and 1-cyclopropyl-piperazine (34 mg, 0.27 mmol) were coupled using the procedure described in example 1; 1.9) using TOTU instead of HATU as the coupling reagent. The mixture was purified by preparative HPLC. Yield after lyophilization: 71 mg, 40%, colorless, amorphous solid.

MS (ES$^+$): m/e=666.4/668.4, chloro pattern.

Example 5

N—[(S)-1-[5-(5-Chloro-thiophen-2-yl)-isoxazol-3-ylmethyl]-2-(4-cyclopropyl-piperazin-1-yl)-2-oxo-ethyl]-2-difluoromethoxy-3-(2-oxo-piperidin-1-yl)-benzenesulfonamide trifluoro acetate

5.1) 1,3-Dibromo-2-difluoromethoxy-benzene (Intermediate 18)

In analogy to (J. Org. Chem. 2005, 3021-3030):
2,6-dibromo-phenol (25.19 g, 100 mmol) and $K_2CO_3$ (16.59 g, 120 mmol) were dissolved in 180 ml of DMF and 20 ml of water. Sodium chlorodifluoroacetate (24.39 g, 160 mmol) was added and the mixture was heated to 100° C. for 3 hours. After cooling the product was crashed out by the addition of water. Filtration and washing yielded 28.2 g, 93%.

5.2) 1-Benzylsulfanyl-3-bromo-2-difluoromethoxy-benzene (Intermediate 19)

Intermediate 18 (28.08 g, 93 mmol) was converted to Intermediate 19 as described in detail following the procedures in example 3; 3.1).
Yield after chromatography on silica gel: 18.78 g, 59%, oil.

5.3) 1-(3-Benzylsulfanyl-2-difluoromethoxy-phenyl) piperidin-2-one (Intermediate 20)

Intermediate 19 (18.64 g, 54 mmol) and piperidin-2-one (5.89 g, 59.4 mmol) were converted to Intermediate 20 as described in detail following the procedure in example 1; 1.5). Yield: 8.98 g, 46%, crystalline solid from n-heptane-ethyl acetate (4:1)

5.4) 2-Difluoromethoxy-3-(2-oxo-piperidin-1-yl) benzenesulfonyl chloride (Intermediate 21)

Intermediate 20 (2.0 g, 5.5 mmol) was submitted to the chemistry described in step 1.6) of example 1. The crude product was used without purification in the next step.

5.5) (S)-3-[5-(5-Chloro-thiophen-2-yl)-isoxazol-3-yl]-2-[2-difluoromethoxy-3-(2-oxo-piperidin-1-yl)-benzenesulfonylamino]-propionic acid methyl ester (Intermediate 22)

Intermediate 2 (1.577 g, 5.50 mmol) and intermediate 21 (1.868 g, 5.50 mmol) were coupled using the procedure described in example 1; 1.7). After workup the crude product was used without further purification in the next step.

5.6) ((S)-3-[5-(5-Chloro-thiophen-2-yl)-isoxazol-3-yl]-2-[2-difluoromethoxy-3-(2-oxo-piperidin-1-yl)-benzenesulfonylamino]-propionic acid (Intermediate 23)

Intermediate 22 (2.6 g, 4.41 mmol) was saponified using the procedure described in example 1; 1.8). After workup the crude product was used without further purification in the next step.

5.7) N—[(S)-1-[5-(5-Chloro-thiophen-2-yl)-isoxazol-3-ylmethyl]-2-(4-cyclopropyl-piperazin-1-yl)-2-oxo-ethyl]-2-difluoromethoxy-3-(2-oxo-piperidin-1-yl)-benzenesulfonamide trifluoro acetate Intermediate 23 (350 mg, 0.61 mmol) and 1-cyclopropyl-piperazine (77 mg, 0.61 mmol) were coupled using the procedure described in example 1; 1.9) using TOTU instead of HATU as the coupling reagent.

The mixture was purified by preparative HPLC. Yield after lyophilization: 193 mg, 40%, colorless, amorphous solid. MS (ES$^+$): m/e=684.3/686.3, chloro pattern.

Example 6

N-{(S)-1-[5-(5-Chloro-thiophen-2-yl)-isoxazol-3-ylmethyl]-2-oxo-2-[4-(2,2,2-trifluoro-ethyl)-piperazin-1-yl]-ethyl}-2-methyl-3-(2-oxo-pyrrolidin-1-yl)-benzenesulfonamide trifluoro acetate 6.1) 1-Benzylsulfanyl-3-bromo-2-methyl-benzene (Intermediate 24)

Commercially available 1,3-dibromo-2-methyl-benzene (34.52 ml, 0.25 mol) was converted to intermediate 24 according to the procedure described in example 1; 1.4).

After workup the crude product was crystallized from DCM-n-heptane.

Yield: 28.06 g, 38

6.2) 1-(3-Benzylsulfanyl-2-methyl-phenyl)-pyrrolidin-2-one (Intermediate 25)

Intermediate 24 (14.08 g, 48 mmol) and pyrrolidin-2-one (4.9 g, 57.6 mmol) were converted to intermediate 25 as described in example 1; 1.5). The crude product (14.6 g) was used without purification in the next step.

6.3) 2-Methyl-3-(2-oxo-pyrrolidin-1-yl)-benzenesulfonyl chloride (Intermediate 26)

Intermediate 25 (1100 mg, 3.7 mmol) was submitted to the chemistry described in step 1.6 of example 1. The crude product was used without purification in the next step.

6.4) (S)-3-[5-(5-Chloro-thiophen-2-yl)-isoxazol-3-yl]-2-[2-methyl-3-(2-oxo-pyrrolidin-1-yl)-benzenesulfonylamino]-propionic acid methyl ester (Intermediate 27)

Intermediate 2 (942 mg, 3.29 mmol) and intermediate 26 (900 mg, 3.29 mmol) were coupled using the procedure described in example 1; 1.7). After workup the crude product was used without further purification in the next step.

6.5) (S)-3-[5-(5-Chloro-thiophen-2-yl)-isoxazol-3-yl]-2-[2-methyl-3-(2-oxo-pyrrolidin-1-yl)-benzenesulfonylamino]-propionic acid (Intermediate 28)

Intermediate 27 (2.1 g, 4.01 mmol) was saponified using the procedure described in example 1; 1.8). After workup the crude product was used without further purification in the next step.

6.6) N-{(S)-1-[5-(5-Chloro-thiophen-2-yl)-isoxazol-3-ylmethyl]-2-oxo-2-[4-(2,2,2-trifluoro-ethyl)-piperazin-1-yl]-ethyl}-2-methyl-3-(2-oxo-pyrrolidin-1-yl)-benzenesulfonamide trifluoro acetate Intermediate 28 (300 mg, 0.59 mmol) and 1-(2,2,2-trifluoro-ethyl)-piperazine (98 mg, 0.59 mmol) were coupled using the procedure described in example 1; 1.9). The mixture was purified by preparative HPLC. Yield after lyophilization: 250 mg, 55%, colorless, amorphous solid. MS (ES$^+$): m/e=659.9/662.0, chloro pattern.

Example 7

N—[(S)-1-[5-(5-Chloro-thiophen-2-yl)-isoxazol-3-ylmethyl]-2-oxo-2-(3-trifluoromethyl-piperazin-1-yl)-ethyl]-2-methyl-3-(2-oxo-pyrrolidin-1-yl)-benzenesulfonamide trifluoro acetate Intermediate 28 (300 mg, 0.59 mmol) and 2-trifluoromethyl-piperazine (90 mg, 0.59 mmol) were coupled using the procedure described in example 1; 1.9). The mixture was purified by prep. HPLC. Yield after lyophilization: 166 mg, 37%, colorless, amorphous solid. MS (ES$^+$): m/e=646.1/648.1, chloro pattern.

According to the previous examples the following compounds were prepared in close analogy:

| Example No. | Compound | Mass (from LC/MS) | Rt (from LC/MS) (min) | LC/MS Method |
|---|---|---|---|---|
| 8 | N-[(S)-1-[5-(5-Chloro-thiophen-2-yl)-isoxazol-3-ylmethyl]-2-(4-methoxy-piperidin-1-yl)-2-oxo-ethyl]-2-ethyl-3-(3-oxo-morpholin-4-yl)-benzenesulfonamide | 637.31/639.34 | 1.71 | E |
| 9 | N-[(S)-1-[5-(5-Chloro-thiophen-2-yl)-isoxazol-3-ylmethyl]-2-(4-hydroxy-piperidin-1-yl)-2-oxo-ethyl]-2-ethyl-3-(3-oxo-morpholin-4-yl)-benzenesulfonamide | 623.26/625.28 | 1.52 | E |
| 10 | 2-Chloro-N-[(S)-1-[5-(5-chloro-thiophen-2-yl)-isoxazol-3-ylmethyl]-2-(4-methoxy-piperidin-1-yl)-2-oxo-ethyl]-3-(3-oxo-morpholin-4-yl)-benzenesulfonamide | 643.02/645.02 | 1.67 | E |
| 11 | N-[(S)-1-[5-(5-Chloro-thiophen-2-yl)-isoxazol-3-ylmethyl]-2-(4-methoxy-piperidin-1-yl)-2-oxo-ethyl]-5-fluoro-2-methoxy-3-(3-oxo-morpholin-4-yl)-benzenesulfonamide | 657.17/659.18 | 2.09 | M |
| 12 | N-{(S)-2-Azepan-1-yl-1-[5-(5-chloro-thiophen-2-yl)-isoxazol-3-ylmethyl]-2-oxo-ethyl}-5-fluoro-2-methoxy-3-(3-oxo-morpholin-4-yl)-benzenesulfonamide | 641.17/643.18 | 2.32 | M |

-continued

| Example No. | Compound | Mass (from LC/MS) | Rt (from LC/MS) (min) | LC/MS Method |
|---|---|---|---|---|
| 13 | N-[(S)-1-[5-(5-Chloro-thiophen-2-yl)-isoxazol-3-ylmethyl]-2-(4-isopropyl-piperazin-1-yl)-2-oxo-ethyl]-5-fluoro-2-methoxy-3-(2-oxo-piperidin-1-yl)-benzenesulfonamide trifluoro acetate | 668.12/670.17 | 1.36 | E |
| 14 | N-[(S)-1-[5-(5-Chloro-thiophen-2-yl)-isoxazol-3-ylmethyl]-2-((R)-3-hydroxy-pyrrolidin-1-yl)-2-oxo-ethyl]-5-fluoro-2-methoxy-3-(2-oxo-piperidin-1-yl)-benzenesulfonamide | 627.22/629.22 | 1.78 | M |
| 15 | N-[(S)-1-[5-(5-Chloro-thiophen-2-yl)-isoxazol-3-ylmethyl]-2-((R)-3-hydroxy-pyrrolidin-1-yl)-2-oxo-ethyl]-2-difluoromethoxy-3-(2-oxo-piperidin-1-yl)-benzenesulfonamide | 645.26/647.28 | 1.9 | M |
| 16 | N-[(S)-1-[5-(5-Chloro-thiophen-2-yl)-isoxazol-3-ylmethyl]-2-(4-cyclopropyl-piperazin-1-yl)-2-oxo-ethyl]-2-methyl-3-(2-oxo-pyrrolidin-1-yl)-benzenesulfonamide trifluoro acetate | 618.12/620.16 | 2.61 | O |
| 17 | N-[(S)-1-[5-(5-Chloro-thiophen-2-yl)-isoxazol-3-ylmethyl]-2-(4-methyl-piperazin-1-yl)-2-oxo-ethyl]-2-methyl-3-(2-oxo-pyrrolidin-1-yl)-benzenesulfonamide trifluoro acetate | 592.10/594.14 | 2.53 | O |
| 18 | N-{(S)-1-[5-(5-Chloro-thiophen-2-yl)-isoxazol-3-ylmethyl]-2-oxo-2-piperazin-1-yl-ethyl}-2-methyl-3-(2-oxo-pyrrolidin-1-yl)-benzenesulfonamide trifluoro acetate | 578.10/580.13 | 2.51 | O |
| 19 | N-{(S)-1-[5-(5-Chloro-thiophen-2-yl)-isoxazol-3-ylmethyl]-2-[4-(2-hydroxy-ethyl)-piperazin-1-yl]-2-oxo-ethyl}-2-methyl-3-(2-oxo-pyrrolidin-1-yl)-benzenesulfonamide trifluoro acetate | 622.12/624.15 | 2.51 | O |
| 20 | N-[(S)-1-[5-(5-Chloro-thiophen-2-yl)-isoxazol-3-ylmethyl]-2-(4-methyl-3-oxo-piperazin-1-yl)-2-oxo-ethyl]-2-methyl-3-(2-oxo-pyrrolidin-1-yl)-benzenesulfonamide | 606.06/608.10 | 2.5 | O |
| 21 | N-{(S)-1-[5-(5-Chloro-thiophen-2-yl)-isoxazol-3-ylmethyl]-2-[4-(2-methoxy-ethyl)-piperazin-1-yl]-2-oxo-ethyl}-2-methyl-3-(2-oxo-pyrrolidin-1-yl)-benzenesulfonamide trifluoro acetate | 636.10/638.16 | 2.33 | O |

LC/MS spectra were recorded according to the following methods:
Method E: Column: YMC J'shere 33×2 mm, 4 µm
  Solvent: $H_2O$+0.05% TFA: ACN+0.05% TFA 95:5 (0 min) to 5:95 (2.5 min) to 95:5 (3 min)
  MS method: LCT system, 0.33 s scan time for mass 170-1300
Method M: Column: YMC Jsphere 33*2
  Grad AcN+0.05% TFA: $H_2O$+0.05% TFA
  5:95 (0 min) to 95:5 (3.4 min) to 95:5 (4.4 min) (flow 1 ml/min)
  MS method: LCT system TOF MS ES+
Method N: column: YMC Jsphere 33*2
  Grad AcN+0.05% TFA: $H_2O$+0.05% TFA
  2:98 (1 min) to 95:5 (5 min) to 95:5 (6.25 min) (flow 1 ml/min)
  MS method: LCT system TOF MS ES+<MUX96>>:C3:C
Method O: column: Waters XBridge C18 4
  Grad (AcN+0.05% TFA): $H_2O$+0.05% TFA
  5:95 (0 min) to 5:95 (0.3 min) to 95:5 (3.5 min) to 95:5 (4 min)
  MS method: LCT system TOF MS ES+
Pharmacological Testing:
The ability of the compounds of the formulae I or Ia to inhibit thrombin or factor Xa or other enzymes like factor VIIa, plasmin, or trypsin can be assessed by determining the concentration of the compound of the formulae I or Ia that inhibits enzyme activity by 50%, i.e. the 1050 value, which was related to the inhibition constant Ki. Purified enzymes were used in chromogenic assays. The concentration of inhibitor that causes a 50% decrease in the rate of substrate hydrolysis was determined by linear regression after plotting the relative rates of hydrolysis (compared to the uninhibited control) versus the log of the concentration of the compound of formulae I or Ia. For calculating the inhibition constant Ki, the 1050 value was corrected for competition with substrate using the formula $Ki=IC50/\{1+(\text{substrate concentration}/Km)\}$ wherein Km is the Michaelis-Menten constant (Chen and Prusoff, Biochem. Pharmacol. 22 (1973) 3099-3108).
Measurement of F Xa and Thrombin Inhibition:
The claimed substances were tested for F Xa and thrombin inhibition with a chromogenic assay. 8 µl DMSO solution of the compound, 72 µL assay buffer (50 mM TRIS, 150 mM NaCl, 0.1% BSA, pH 7.8) and 20 µL enzyme (human coagulation factor Xa: Haemochrom Diag. Cat. Nr. HFXa, final concentration 380 µM; human thrombin Behring: LOT.-No. 881001) were mixed and incubated for 15 minutes at room temperature in a 96 well microtiter plate. The enzyme reaction was started with 100 μL substrate (F Xa: S-2765, Chromogenix/Haemochrom Cat. Nr. 41249; thrombin: S-2366, Chromogenix/Haemochrom Cat. Nr. 41222 both in a final concentration of 200 μM). The time course of the reaction was monitored at 405 nm in a microtiter plate reader (SpectraMax plus 384; Molecular Devices Inc.) for 15 minutes.

The Ki was calculated from the mean of duplicates from a dilution series of the compound by the reader according to the Cheng Prusoff formula Ki=IC50/(1+(S/Km).

The results (inhibition constants Ki Thrombin and FXa in mikro M [μM]) for inhibition of thrombin and factor Xa are shown in Table 1.

TABLE 1

| Example | Ki (Thrombin, μM) | Ki (Xa, μM) |
|---|---|---|
| 1 | 0.00035 | 0.013 |
| 2 | 0.007 | 0.083 |
| 3 | 0.268 | 0.904 |
| 4 | 0.029 | 0.006 |
| 5 | 0.094 | 0.033 |
| 6 | 0.014 | 0.00072 |
| 7 | 0.00079 | 0.00044 |

What is claimed is:
1. A compound of formula Ia,

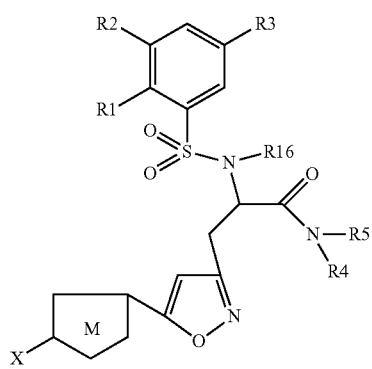

wherein

is a thiophenyl residue,
X is halogen;
R1 and R3 are selected from H, halogen, $(C_1-C_4)$-alkyl, and $-O(C_1-C_4)$-alkyl, wherein alkyl can be unsubstituted or substituted once, two, or three times by halogen;
R2 is a 5- or 6-membered lactam ring optionally substituted one, two, or three times by R8;
R4 and R5 are the same or different and are independently of one another
1) hydrogen atom,
2) $-(C_1-C_6)$-alkyl, wherein alkyl is unsubstituted or mono-, di- or trisubstituted independently of one another by R7,
3) $-(C_0-C_6)$-alkylene-$(C_3-C_8)$-cycloalkyl,
4) $-SO_t-R10$, wherein t is 1 or 2,
5) $-(C_0-C_6)$-alkylene-aryl, wherein aryl is selected from the group consisting of phenyl, naphthyl, biphenylyl, anthryl, and fluorenyl, and alkylene and aryl independently from one another are unsubstituted or mono-, di- or trisubstituted by R7,
6) $-(C_1-C_3)$-fluoroalkyl,
7) $-O-(C_1-C_4)$-alkyl or
8) $-(C_0-C_6)$-alkylene-heterocyclyl, wherein heterocyclyl is selected from the group consisting of acridinyl, azabenzimidazolyl, azaspirodecanyl, azepinyl, azetidinyl, aziridinyl, benzimidazolyl, 1,3-benzodioxolyl, benzofuranyl, benzothienyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phenylpyridyl, phthalazinyl, piperazinyl, piperidinyl, pteridinyl, purinyl, pyranyl, pyrazinyl, pyrazolidinyl, pyrazolinyl, pyrazolyl, pyridazinyl, pyridoimidazolyl, pyridooxazolyl, pyridopyrimidinyl, pyridothiazolyl, pyridothienyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinolyl, quinoxalinyl, quinuclidinyl, tetrahydrofuranyl, tetrahydroisoquinolinyl, tetrahydroquinolinyl, 1,4,5,6-tetrahydro-pyridazinyl, tetrahydropyranyl, tetrahydropyridinyl, tetrahydro-thiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,4-triazolyl, 1,2,5-triazolyl, 1,3,4-triazolyl and xanthenyl, and alkylene and heterocyclyl independently from one another are unsubstituted or mono-, di- or trisubstituted by R7, provided that R4 and R5 are not each a hydrogen atom, or R4 and R5 together with the nitrogen atom to which they are bonded form a 4- to 10-membered mono- or bicyclic heterocyclic ring selected from 2-oxa-5-aza-bicyclo [2.2.1]heptane, azepane, azepine, azetidine, 2,5-diazabicyclo[2.2.1]heptane, 1,4-diazepane, 1,2-diazepine, 1,3-diazepine, 1,4-diazepine, 2,3-dihydro-1H-isoindole, 2,3-dihydro-1H-pyrrolo[3,4-c]pyridine, 6,7-dihydro-5H-pyrrolo[3,4-b]pyridine, 5,6-dihydro-4H-pyrrolo[3,4-d]thiazole, dioxazole, dioxazine, imidazole, imidazoline, imidazolidine, isothiazole, isothiazolidine, isothiazoline, isoxazole, isoxazoline, isoxazolidine, 2-isoxazoline, morpholine, octahydro-pyrido[1,2-a]

pyrazine, octahydro-pyrrolo[3,4-b]pyridine, octahydro-pyrrolo[1,2-a]pyrazine, [1,4]oxazepane, 1,4-oxazepine, oxazole, piperazine, piperidine, piperidinone, pyrazine, pyrazole, pyrazoline, pyrazolidine, pyridazine, pyridine, pyridone, pyrimidine, pyrrole, pyrrolidine, pyrrolidinone, pyrroline, 4,5,6,7-tetrahydro-1H-imidazo[4,3-c]pyridine, tetrahydropyridine, 1,4,5,6-tetrahydro-pyrrolo[3,4-c]pyrazole, 4,5,6,7-tetrahydro-thiazolo[5,4-c]pyridine, 5,6,7,8-tetrahydro-[1,2,4]triazolo[4,3-a]pyrazine, 4,5,6,7-tetrahydro-thieno[3,2-c]pyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole and 1,2,4-triazole, wherein said heterocyclic ring is unsubstituted or mono-, di- or trisubstituted independently of one another by R7;

R6 is: 1) heterocyclyl, wherein heterocyclyl is as defined above and is un-substituted or mono-, di- or tri substituted independently of one another by R8, or
2) aryl, as defined above, wherein aryl is unsubstituted or mono-, di-, or tri-substituted independently of one another by R8, R7 is halogen, —NO$_2$, =O, —CF$_3$, —(C$_0$-C$_3$)-alkylene-C(O)—O—R10, —C(O)—R10, —CN, —OH, —NH$_2$, —C(O)—N(R10)-R20, —N(R10)-R20, =F$_2$, —O—(C$_1$-C$_3$)-fluoroalkyl, —(C$_0$-C$_4$)-alkylene-(C$_1$-C$_3$)-fluoroalkyl, —(C$_0$-C$_3$)-alkylene-(C$_3$-C$_8$)-cycloalkyl, —(C$_1$-C$_8$)-alkyl, wherein alkyl is unsubstituted or mono-, di- or trisubstituted independently of one another by halogen, NH$_2$, —OH or —O—(C$_1$-C$_6$)-alkyl, —O—(C$_1$-C$_6$)-alkyl, wherein alkyl is unsubstituted or mono-, di- or trisubstituted independently of one another by halogen, NH$_2$, —OH or a methoxy residue, or —(C$_0$-C$_3$)-alkylene-heterocyclyl, wherein heterocyclyl is as defined above and is unsubstituted mono-, di- or trisubstituted independently of one another by R10;

R8 is halogen, —NO$_2$, —CN, =O, —OH, —CF$_3$, —C(O)—O—R10, —(C$_3$-C$_8$)-cycloalkyl, —(C$_0$-C$_3$)-alkylene-O—R10, —Si—(CH$_3$)$_3$, —N(R10)-S(O)$_u$—R10, wherein u is 1 or 2, —S—R10, —SO$_r$—R10, wherein r is 1 or 2, —S(O)$_v$—N(R10)-R20, wherein v is 1 or 2, —C(O)—R10, —(C$_1$-C$_8$)-alkyl, —(C$_1$-C$_8$)-alkoxy, phenyl, phenyloxy-, —O—CF$_3$, —(C$_1$-C$_3$)-fluoroalkyl, —NH—C(O)—NH—R6 or —NH—C(O)—O—R10;

R10 and R20 are the same or different and are independently of one another hydrogen atom, halogen, —(C$_1$-C$_6$)-alkyl, —(C$_0$-C$_4$)-alkyl-OH, —(C$_1$-C$_3$)-fluoroalkyl, —(C$_0$-C$_4$)-alkyl-O—(C$_1$-C$_4$)-alkyl, —(C$_0$-C$_5$)-alkyl-(C$_3$-C$_8$)-cycloalkyl, —(C$_0$-C$_2$)-alkylene-aryl, wherein aryl is as defined above and aryl is unsubstituted or substituted one, two or three times independent of each other by —(C$_1$-C$_6$)-alkyl, halogen or —(C$_3$-C$_8$)-cycloalkyl, or —(C$_0$-C$_2$)-alkylene-heterocyclyl, wherein heterocyclyl is as defined above and heterocyclyl is unsubstituted or substituted one, two or three times independent of each other by —(C$_1$-C$_6$)-alkyl, halogen or —(C$_3$-C$_8$)-cycloalkyl; and R16 is selected from hydrogen atom, —OH, and —O—(C$_1$-C$_4$)-alkyl;

or a stereoisomeric form thereof, or a physiologically tolerable salt of any of these.

2. A compound of claim 1, wherein
R4 and R5 are the same or different and are independently of one another hydrogen atom or —(C$_0$-C$_4$)-alkylene-(C$_3$-C$_6$)-cycloalkyl, provided that R4 and R5 are not each a hydrogen atom, or
R4 and R5 together with the nitrogen atom to which they are bonded form a 4- to 10-membered mono- or bicyclic heterocyclic ring selected from 2-oxa-5-aza-bicyclo[2.2.1]heptane, azepane, azepine, azetidine, 2,5-diaza-bicyclo[2.2.1]heptane, 1,4-diazepane, 1,2-diazepine, 1,3-diazepine, 1,4-diazepine, 2,3-dihydro-1H-isoindole, 2,3-dihydro-1H-pyrrolo[3,4-c]pyridine, 6,7-dihydro-5H-pyrrolo[3,4-b]pyridine, 5,6-dihydro-4H-pyrrolo[3,4-d]thiazole, dioxazole, dioxazine, imidazole, imidazoline, imidazolidine, isothiazole, isothiazolidine, isothiazoline, isoxazole, isoxazoline, isoxazolidine, 2-isoxazoline, morpholine, octahydro-pyrido[1,2-a]pyrazine, octahydro-pyrrolo[3,4-b]pyridine, octahydro-pyrrolo[1,2-a]pyrazine, [1,4]oxazepane, 1,4-oxazepine, oxazole, piperazine, piperidine, piperidinone, pyrazine, pyrazole, pyrazoline, pyrazolidine, pyridazine, pyridine, pyridone, pyrimidine, pyrrole, pyrrolidine, pyrrolidinone, pyrroline, 4,5,6,7-tetrahydro-1H-imidazo[4,3-c]pyridine, tetrahydropyridine, 1,4,5,6-tetrahydro-pyrrolo[3,4-c]pyrazole, 4,5,6,7-tetrahydro-thiazolo[5,4-c]pyridine, 5,6,7,8-tetrahydro-[1,2,4]triazolo[4,3-a]pyrazine, 4,5,6,7-tetrahydro-thieno[3,2-c]pyridine, tetrazine, tetrazole, thiazole, thiadiazole, thia-zolidine, thiazoline, thiomorpholine, thiophene, 1,2,3-triazine, 1,2,4-triazine, 1,3,5-triazine, 1,2,3-triazole and 1,2,4-triazole, wherein said heterocyclic ring is unsubstituted or mono-, di- or trisubstituted independently of one another by R7, R7 is halogen, =O, —(C$_0$-C$_3$)-alkylene-C(O)—O—R10, —C(O)—R10, —OH, —NH$_2$, =F$_2$, —O—(C$_1$-C$_3$)-fluoroalkyl, —(C$_0$-C$_3$)-alkylene-(C$_1$-C$_3$)-fluoroalkyl, —(C$_1$-C$_6$)-alkyl, wherein alkyl is unsubstituted or mono-, di- or trisubstituted independently of one another by halogen, NH$_2$, —OH or —O—(C$_1$-C$_6$)-alkyl, —(C$_0$-C$_3$)-alkylene-(C$_3$-C$_8$)-cycloalkyl or —O—(C$_1$-C$_6$)-alkyl, wherein alkyl is unsubstituted or mono-, di- or trisubstituted independently of one another by halogen, NH$_2$, —OH or a methoxy residue;

R8 is halogen, =O or —(C$_1$-C$_4$)-alkyl;

R10 and R20 are the same or different and are independently of one another hydrogen atom, halogen, —(C$_1$-C$_6$)-alkyl, or —(C$_0$-C$_3$)-alkyl-(C$_3$-C$_6$)-cycloalkyl; and R16 is hydrogen atom.

3. A compound as claimed in claim 1, which is selected from the group consisting of:

N-{(S)-2-azepan-1-yl-1-[5-(5-chloro-thiophen-2-yl)-isoxazol-3-ylmethyl]-2-oxo-ethyl}-2-ethyl-3-(3-oxo-morpholin-4-yl)-benzene-sulfonamide, N-{(S)-2-azepan-1-yl-1-[5-(5-chloro-thiophen-2-yl)-isoxazol-3-ylmethyl]-2-oxo-ethyl}-2-chloro-3-(3-oxo-morpholin-4-yl)-benzenesulfonamide, (S)-3-[5-(5-chloro-thiophen-2-yl)-isoxazol-3-yl]-N-cyclopropylmethyl-2-[5-fluoro-2-methoxy-3-(2-oxo-piperidin-1-yl)-benzenesulfonylamino]-propionamide, N—[(S)-1-[5-(5-chloro-thiophen-2-yl)-isoxazol-3-ylmethyl]-2-(4-cyclopropyl-piperazin-1-yl)-2-oxo-ethyl]-5-fluoro-2-methoxy-3-(2-oxo-piperidin-1-yl)-benzenesulfonamide, N—[(S)-1-[5-(5-chloro-thiophen-2-yl)-isoxazol-3-ylmethyl]-2-(4-cyclopropyl-piperazin-1-yl)-2-oxo-ethyl]-2-difluoromethoxy-3-(2-oxo-piperidin-1-yl)-benzenesulfonamide, N-{(S)-1-[5-(5-chloro-thiophen-2-yl)-isoxazol-3-ylmethyl]-2-oxo-2-[4-(2,2,2-trifluoro-ethyl)-piperazin-1-yl]-ethyl}-2-methyl-3-(2-oxo-pyrrolidin-1-yl)-benzenesulfonamide, N—[(S)-1-[5-(5-chloro-thiophen-2-yl)-isoxazol-3-ylmethyl]-2-oxo-2-(3-trifluoromethyl-piperazin-1-yl)-ethyl]-2-methyl-3-(2-oxo-pyrrolidin-1-yl)-benzenesulfonamide, N—[(S)-1-[5-(5-chloro-thiophen-2-yl)-isoxazol-3-ylmethyl]-2-(4-methoxy-piperidin-1-yl)-2-oxo-ethyl]-2-ethyl-3-(3-oxo-morpholin-4-yl)-benzenesulfonamide, N—[(S)-1-[5-(5-chloro-thiophen-2-yl)-isoxazol-3-ylmethyl]-2-(4-hydroxy-piperidin-1-yl)-2-oxo-ethyl]-2-ethyl-3-(3-oxo-morpholin-4-yl)-benzenesulfonamide, 2-chloro-N—[(S)-1-[5-(5-chloro-thiophen-2-yl)-isoxazol-3-ylmethyl]-2-(4-methoxy-piperidin-1-yl)-2-oxo-ethyl]-3-(3-oxo-morpholin-4-yl)-benzenesulfonamide, N—[(S)-1-[5-(5-chloro-thiophen-2-yl)-isoxazol-3-ylmethyl]-2-(4-methoxy-piperidin-1-yl)-2-oxo-ethyl]-5-fluoro-2-methoxy-3-(3-oxo-morpholin-4-yl)-benzenesulfonamide, N-{(S)-2-azepan-1-yl-1-[5-(5-chloro-thiophen-2-yl)-isoxazol-3-ylmethyl]-2-oxo-ethyl}-5-fluoro-2-methoxy-3-(3-oxo-morpholin-4-yl)-benzenesulfonamide, N—[(S)-1-[5-(5-chloro-thiophen-2-yl)-isoxazol-3-ylmethyl]-2-(4-isopropyl-piperazin-1-yl)-2-oxo-ethyl]-5-fluoro-2-methoxy-3-(2-oxo-piperidin-1-yl)-benzenesulfonamide, N—[(S)-1-[5-(5-chloro-thiophen-2-yl)-isoxazol-3-ylmethyl]-2-((R)-3-hydroxy-pyrrolidin-1-yl)-2-oxo-ethyl]-5-fluoro-2-methoxy-3-(2-oxo-piperidin-1-yl)-benzenesulfonamide, N—[(S)-1-[5-(5-chloro-thiophen-2-yl)-isoxazol-3-ylmethyl]-2-((R)-3-hydroxy-pyrrolidin-1-yl)-2-oxo-ethyl]-2-difluoromethoxy-3-(2-oxo-piperidin-1-yl)-benzenesulfonamide, N—[(S)-1-[5-(5-chloro-thiophen-2-yl)-isoxazol-3-ylmethyl]-2-(4-cyclopropyl-piperazin-1-yl)-2-oxo-ethyl]-2-methyl-3-(2-oxo-pyrrolidin-1-yl)-benzenesulfonamide, N—[(S)-1-[5-(5-chloro-thiophen-2-yl)-isoxazol-3-ylmethyl]-2-(4-methyl-piperazin-1-yl)-2-oxo-ethyl]-2-methyl-3-(2-oxo-pyrrolidin-1-yl)-benzenesulfonamide, N-{(S)-1-[5-(5-chloro-thiophen-2-yl)-isoxazol-3-ylmethyl]-2-oxo-2-piperazin-1-yl-ethyl}-2-methyl-3-(2-oxo-pyrrolidin-1-yl)-benzenesulfonamide, N-{(S)-1-[5-(5-chloro-thiophen-2-yl)-isoxazol-3-ylmethyl]-2-[4-(2-hydroxy-ethyl)-piperazin-1-yl]-2-oxo-ethyl}-2-methyl-3-(2-oxo-pyrrolidin-1-yl)-benzenesulfon-amide, N—[(S)-1-[5-(5-chloro-thiophen-2-yl)-isoxazol-3-ylmethyl]-2-(4-methyl-3-oxo-piperazin-1-yl)-2-oxo-ethyl]-2-methyl-3-(2-oxo-pyrrolidin-1-yl)-benzenesulfonamide, and N-{(S)-1-[5-(5-chloro-thiophen-2-yl)-isoxazol-3-ylmethyl]-2-[4-(2-methoxy-ethyl)-piperazin-1-yl]-2-oxo-ethyl}-2-methyl-3-(2-oxo-pyrrolidin-1-yl)-benzenesulfonamide.

4. A compound of claim 1, wherein X is Cl.

5. A compound of claim 1, wherein said 5- or 6-membered lactam ring of R2 is selected from:

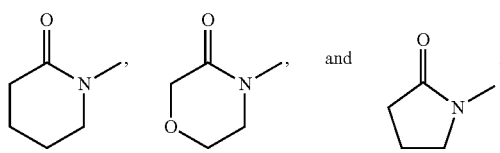

6. A compound of claim 1, wherein R4 and R5 together with the nitrogen atom to which they are bonded form a 4- to 10-membered mono- or bicyclic heterocyclic ring selected from 2-oxa-5-aza-bicyclo[2.2.1]heptane, azepane, azepine, azetidine, 2,5-diaza-bicyclo[2.2.1]heptane, 1,4-diazepane, 1,2-diazepine, 1,3-diazepine, 1,4-diazepine, 2,3-dihydro-1H-isoindole, 2,3-dihydro-1H-pyrrolo[3,4-c]pyridine, 6,7-dihydro-5H-pyrrolo[3,4-b]pyridine, 5,6-dihydro-4H-pyrrolo[3,4-d]thiazole, dioxazole, dioxazine, imidazole, imidazoline, imidazolidine, isothiazole, isothiazolidine, isothiazoline, isoxazole, isoxazoline, isoxazolidine, 2-isoxazoline, morpholine, octahydro-pyrido[1,2-a]pyrazine, octahydro-pyrrolo[3,4-b]pyridine, octahydro-pyrrolo[1,2-a]pyrazine, [1,4]oxazepane, 1,4-oxazepine, oxazole, piperazine, piperidine, piperidinone, pyrazine, pyrazole, pyrazoline, pyrazolidine, pyridazine, pyridine, pyridone, pyrimidine, pyrrole, pyrrolidine, pyrrolidinone, pyrroline, 4,5,6,7-tetrahydro-1H-imidazo[4,3-c]pyridine, tetra-hydropyridine, 1,4,5,6-tetrahydro-pyrrolo[3,4-c]pyrazole, 4,5,6,7-tetrahydro-thiazolo[5,4-c]pyridine, 5,6,7,8-tetrahydro-[1,2,4]triazolo[4,3-a]pyrazine, 4,5,6,7-tetrahydro-thieno[3,2-c]pyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole and 1,2,4-triazole, wherein said heterocyclic ring is unsubstituted or mono-, di- or trisubstituted independently of one another by R7.

7. A compound of claim 1, wherein said 4- to 10-membered mono- or bicyclic heterocyclic ring is selected from azepane, azepine, 1,4-diazepane, 1,2-diazepine, 1,3-diazepine, 1,4-diazepine, imidazole, imidazoline, imidazolidine, morpholine, [1,4]oxazepane, 1,4-oxazepine, oxazole, piperazine, piperidine, piperidinone, pyrazine, pyrazole, pyrazoline, pyrazolidine, pyridazine, pyridine, pyridone, pyrimidine, pyrrole, pyrrolidine, pyrrolidinone, pyrroline, tetrahydropyridine, 1,2,3-triazine, 1,2,4-triazine, 1,3,5-triazine, 1,2,3-triazole and 1,2,4-triazole, wherein said heterocyclic ring is unsubstituted or mono-, di- or trisubstituted independently of one another by R7.

8. A compound of claim 1, wherein R1 and R3 are selected from H, halogen, $(C_1-C_4)$-alkyl, and —$O(C_1-C_4)$-alkyl, wherein alkyl can be unsubstituted or substituted one, two, or three times by F.

9. A compound of claim 1, wherein R1 and R3 are selected from H, halogen, $(C_1-C_3)$-alkyl, and —$O(C_1-C_3)$-alkyl, wherein alkyl can be unsubstituted or substituted one, two, or three times by halogen.

10. A compound of claim 1, wherein R1 and R3 are selected from H, halogen, $(C_1-C_3)$-alkyl, and —$O(C_1-C_3)$-alkyl, wherein alkyl can be unsubstituted or substituted one, two, or three times by F.

11. A compound of claim 1, wherein R1 and R3 are selected from H, halogen, $(C_1-C_2)$-alkyl, and —$O(C_1-C_2)$-alkyl, wherein alkyl can be unsubstituted or substituted one, two, or three times by halogen.

12. A compound of claim 1, wherein R1 and R3 are selected from H, halogen, $(C_1-C_2)$-alkyl, and —$O(C_1-C_2)$-alkyl, wherein alkyl can be unsubstituted or substituted one, two, or three times by F.

13. A pharmaceutical composition, comprising at least one compound as claimed in claim 1 and a pharmaceutically acceptable carrier.

14. A process for the preparation of a compound of formula Ia as claimed in claim 1, comprising linking a compound of formula II with a compound of formula IV

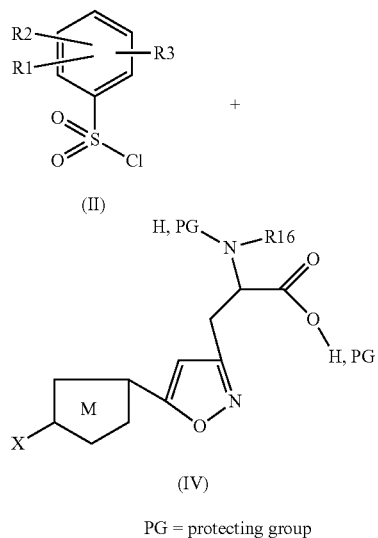

PG = protecting group wherein R1, R2, R3, R16, X and M are as defined in claim 4, by forming a sulfonamide bond between a sulfonyl chloride group of the compound of formula II and an amino group of the compound of formula IV to form a compound of formula V

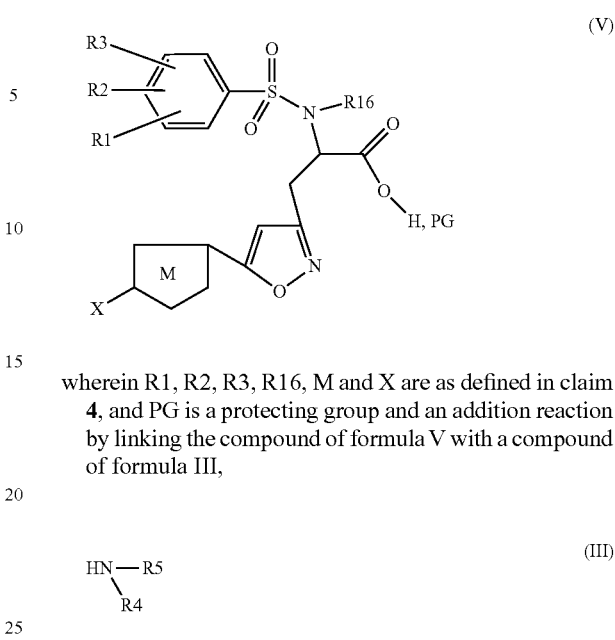

wherein R1, R2, R3, R16, M and X are as defined in claim 4, and PG is a protecting group and an addition reaction by linking the compound of formula V with a compound of formula III, $$HN-R5$$
$$|$$
$$R4$$

(III)

wherein R4 and R5 are as defined in claim 4, by forming an amide bond between a carboxylic acid group of formula V and an amino group of formula III to form a compound of formula Ia.

* * * * *